US005654167A

United States Patent [19]

Gabay et al.

[11] Patent Number: 5,654,167
[45] Date of Patent: Aug. 5, 1997

[54] ANTIMICROBIAL PROTEINS, COMPOSITIONS CONTAINING SAME AND USES THEREOF

[75] Inventors: Joelle E. Gabay, New York; Carl F. Nathan, Larchmont, both of N.Y.

[73] Assignees: Cornell Research Foundation, Inc., Ithaca; Rockefeller University, New York, both of N.Y.

[21] Appl. No.: 208,181

[22] Filed: Mar. 8, 1994

Related U.S. Application Data

[63] Continuation of Ser. No. 677,371, Mar. 26, 1991, abandoned, which is a continuation-in-part of Ser. No. 276,136, Nov. 25, 1988, abandoned, which is a continuation-in-part of Ser. No. 125,684, Nov. 25, 1987, Pat. No. 5,087,569, which is a continuation-in-part of Ser. No. 106,524, Oct. 6, 1987, Pat. No. 5,126,257, which is a continuation-in-part of Ser. No. 935,509, Nov. 26, 1986, abandoned.

[30] Foreign Application Priority Data

Nov. 25, 1987 [EP] European Pat. Off. ............. 87117408

[51] Int. Cl.$^6$ ..................... C12P 21/02; C12P 19/34; C12N 15/06; C12N 15/12
[52] U.S. Cl. ................. 435/69.1; 536/23.1; 536/23.5; 435/172.3; 435/320.1; 435/252.3; 435/372; 935/9; 935/24; 935/70
[58] Field of Search ................. 536/23.6, 23.2, 536/23.5; 435/320.1, 172.3, 240.2, 252.3, 69.1, 69.6, 91.1, 183; 935/9, 11, 14, 22, 23, 27, 32, 60, 70

[56] References Cited

U.S. PATENT DOCUMENTS

| | | | |
|---|---|---|---|
| 4,394,443 | 7/1983 | Weissman et al. | 435/6 |
| 4,468,464 | 8/1984 | Cohen et al. | 435/320.1 |
| 4,675,285 | 6/1987 | Clark et al. | 435/6 |
| 4,727,028 | 2/1988 | Santerre et al. | 435/240.2 |
| 5,091,303 | 2/1992 | Amaout et al. | 435/7.24 |

OTHER PUBLICATIONS

Morgan, J.G., (1991) "Cloning the cDNA for the Serine Protease Homolog CAP 37/Azurocidin, A Microbicidal and Chemotactic Protein from Human Granulocytes," The J. of Immunology 147: 3210–3214 (Exhibit 1).
Campanelli, D. et al., (1990) "Azurocidin and a Homologous Serine Protease from Neutrophils, Differential Antimicrobial and Proteolytic Properties" J. Clin. Invest. 85: 904–915 (Exhibit 2).
Pereira, H. A. et al., (1990) "CAP37, a Human Neutrophil–Derived Chemotactic Factor with Monocyte Specific Activity" J. Clin. Invest. 85 (5) 1468–1476 (Exhibit 3) —Abstract only.
Pereira, H.A. (1990) "CAP 37, a 37 kD Human Neutrophil Granule Cationic Protein Shares Homology with Inflammatory Proteinases" 46 (3): 189–196 (Exhibit 4) Abstract Only.

Hanson, R.D. et al., (1990) "A Cluster of Hematopoietic Serine Protease Genes Is Found on the Same Chromosomal Band as the Human Alpha/Delta T–Cell Receptor Locus" Proc. Natl. Acad. Sci. 87 (3): 960–963 U.S.A. (Exhibit 5) Abstract only.
Campanelli, D. et al., (1990) "Cloning of cDNA for Proteinase 3: A Serine Protease, Antibiotic, and Autoantigen from Human Neutrophils" J. Exp. Med. 172:1709–1715 (Exhibit 6).
Rao, N.V. et al., (1991) "Characterization of Proteinase–3 (PR–3), a Neutrophil Serine Proteinase" J. of Biol. Chem. 266 (15):9540–9548 (Exhibit 7).
Bories, D. et al., (1989) "Down–Regulation of a Serine Protease, Myeloblastin, Causes Growth Arrest and Differentiation of Promyelocytic Leukemia Cells" 59:959–968 (Exhibit 8).
Sturrock, A.B. et al., (1992) "Structure, Chromosomal Assignment, and Expression of the Gene for Proteinase–3, the Wegener's Granulomatosis Autoantigen" J. of Biol. Chem. 267 (29):21193–21199 (Exhibit 9).
Kao, R.C. et al., (1988) "Proteinase 3 A Distinct Human Polymorphonuclear Leukocyte Proteinase that Produces Emphysema in Hamsters" J. Clin. Invest. 82:1963–1973 (Exhibit 10).
Kam, C–M et al., (1992) "Substrate and Inhibitor Studies on Proteinase 3" FEBS Letters 297 (1,2):119–123 (Exhibit 11).
McGrogan, M. et al., (1988) "Isolation of a Complementary DNA Clone Encoding a Precursor to Human Eosinophil Major Basic Protein" J. Exp. Med. 168:2295–2308 (Exhibit 12).
Hastie, A. T. et al. (1987) "The Effect of Purified Human Eosinophil Major Basic Protein on Mammalian Ciliary Activity" Am. Rev. Respir. Dis. 135:848–853 (Exhibit 13).
Wasmoen, T. L. et al., (1988) "Biochemical and Amino Acid Sequence Analysis of Human Eosinophil Granule Major Basic Protein" J. of Biol. Chem. 263 (25): 12559–12563 (Exhibit 14).
Gleich, G. J. et al., (1979) "Cytotoxic Properties of the Eosinophil Major Basic Protein" J. of Immun. 123 (6):2925–2927 (Exhibit 15).
Weller, P. F. et al. (1988) "Eosinophil Granule Cationic Proteins: Major Basic Protein is Distinct from the Smaller Subunit of Eosinophil Peroxidase" J. of Leukocyte Biol. 43:1–4 (Exhibit 16).

(List continued on next page.)

*Primary Examiner*—Christopher S. F. Low
*Attorney, Agent, or Firm*—Karl Bozicevic; Carol L. Francis; Fish & Richardson P.C.

[57] ABSTRACT

The present invention provides purified polypeptides useful as antimicrobial agents. These polypeptides comprise human polymorphonuclear leukocyte polypeptides having molecular weights of about 25,000 daltons, 29,000 daltons and 54,000 daltons. These polypeptides have respiratory burst-independent, antibacterial activity at a pH from about 5.0 to about 8.0, at calcium ion concentrations up to about 10 mM, and at sodium chloride concentrations up to about 0.3M.

10 Claims, 21 Drawing Sheets

OTHER PUBLICATIONS

Butterworth, A. E. et al. (1979) "Damage to Schistosomula of *Schistosoma Mansoni* Induced Directly by Eosinophil Major Basic Protein" J. of Immun. 122 (1):221–229 (Exhibit 17).

Frigas, E. et al. (1986) "The Eosinophil and the Pathophysiology of Asthma" J. Allergy Clin. Immunol. 77 (4):527–537 (Exhibit 18).

Weiler, D. et al. (1989) "Mast Cells in Carnoy's Fixed Tissue Stain Positively for Eosinophil Major Basic Protein (MBP)" Federation Proceedings Abstract 3612 (Exhibit 19).

Wasmoen, T.L. et al. (1987) "Biochemical and Amino Acid Sequence Analysis of Eosinophil Granule Major Basic Protein" Federation Proceedings Abstract 3577 (Exhibit 20).

Slifman, N. et al. (1987) "Eosinophil–Derived Neurotoxin and Eosinophil Protein–X: Comparison of Physicochemical, Immunologic and Enzymatic Properties" Federation Proceedings Abstract 3578 (Exhibit 21).

O'Donnell, M. C. et al. (1983) "Activation of Basophil and Mast Cell Histamine Release by Eosinophil Granule Major Basic Protein" J. Exp. Med. 157:1981–1991 (Exhibit 22).

Wasmoen, T. L. et al. (1987) "Increases of Plasma Eosinophil Major Basic Protein Levels Late in Pregnancy Predict Onset of Labor" Proc. Natl. Acad. Sci. USA 84:3029–3032 (Exhibit 23).

Peters, M. S. et al. (1987) "Extracellular Deposition of Eosinophil Granule Major Protein In Pressure Urticaria" J. Am. Acad. Dermatol. 16 (3) (I):513–517 (Exhibit 24).

Jenne et al., 1990, Nature 346, p. 520.

Froohney, I.R. 1983. in: *Culture of Animal Cells A Manual of Basic Technique*. Alan R. Lins, Inc. NY. p. 167.

Young et al. 1983 Proc. Natl. Acad Sci. USA 80, 1194–1198.

Suggs et al. 1981. Proc. Natl. Acad. Sci. USA. 78, 6613–6617.

Thilly (ed.) 1986. in: *Mammalian Cell Technology*. Butterworths., Boston pp. 63–89.

Maddox et al. 1984. J. Exp. Med. 160, 29–41.

Fischkoff et al. 1984. J. Exp. Med. 160, 179–196.

Gabay et al. 1989. Proc. Natl. Acad. Sci. USA 86, 5610–5614.

Heck et al. 1986. Anal. Biochem. 158, 217–227.

Sequence Comparison (Alignment) of sequence ident. No. 23, with that of Barker et al. (J. Exp. Med. vol. 68, of record).

Ohlsson et al. 1990. Biol. Chem. Hoppe–Seyler. 371, 549–555.

Klein, J. 1982 in: Immunology. The Science of Self–Nonself Discrimination. John Wiley and Sons. New York p. 101.

Okayama et al. (1983) Molec. Cell. Biol. 3, 280–289.

Heron, E. J. (1984) Am. Biotechnol Lab. 2, 52–54, 56, 58–59.

Hunkapiller et al. (1983) Meth. Enzymol. 91, 399–413.

Wallace et al. (1981) Nuc. Acids Res. 9, 879–894.

Barker et al. J. Exp. Med. 168, 1493–1498.

Collins et al. (1977) Nature 270, 347–349.

Rest et al. (1978) Infec. Immun. 19, 131–137.

Maniatis et al. (eds.) *Molecular Cloning: A Laboratory Manual*. Cold Spring Harbor Laboratory, Cold Spring Harbor, NY. pp. 188–199.

AZUROPHIL GRANULE-DERIVED PROTEINS

| Peak | Identity | 1 | | | | 5 | | | | | 10 | | | | | 15 |
|---|---|---|---|---|---|---|---|---|---|---|---|---|---|---|---|---|
| 1 | | C | Y | C | R | I | F | A | C | I | A | G | E | R | R | Y |
| 2 | | V | X | X | X | R | L | V | F | X | R | R | T | G | L | R |
| 3 | | X | P | P | Q | F | T | R | A | Q | W | F | A | I | Q | H |
| 4 | | I | I | G | G | R | E | S | R | P | H | S | R | P | Y | M |
| 5a | | K | V | F | E | R | X | E | L | A | R | T | L | K | R | L |
| 5b | | T | C | R | Y | L | L | V | R | S | L | Q | T | F | S | Q |
| 6 | | I | V | G | G | R | K | A | R | P | R | Q | F | P | F | L |
| 7 | | I | V | G | G | H | E | A | X | X | P | S | D | P | Y | M |
| 8a | | V | N | C | E | T | S | C | V | Q | Q | P | P | C | F | P |
| 8b | | I | V | G | G | R | R | A | R | P | H | A | X | P | X | M |
| 9 | | V | N | P | G | V | V | V | R | I | S | Q | K | G | L | D |
| 9b | | T | C | R | Y | L | L | V | R | S | L | Q | T | F | S | Q |

```
              10                    20                    30                    40
GGG AAG ATC TAA AGA CCC AGG AAG GTC TCT GGG TGG GAT AAA GCC AAG 100                   110                   120                   130
TCT GCT CTT CAT CTA AGG TCT GAG ACT TCC ACC TTT GAG ACC CCT TTG
Ser Ala Leu His Leu Arg Ser Glu Thr Ser Thr Phe Glu Thr Pro Leu 190                   200                   210                   220
GAG ATG GAG GAG ACC CCT TGC AGG GAG CTG GAG GAA GAG GAG TGG
Glu Met Glu Glu Thr Pro Cys Arg Glu Leu Glu Glu Glu Glu Trp 280                   290                   300                   310
GAG TCT ATC TCA GTG CCA GAT ATG GTG GAC AAA AAC CTT ACG TGT CCT
Glu Ser Ile Ser Val Pro Asp Met Val Asp Lys Asn Leu Thr Cys Pro 370                   380                   390                   400
CAG ACC TGC CTC TAC CTC CTG GTG AGA AGT CTT CAG ACG TTT AGT CAA
Gln Thr Cys Arg Tyr Leu Leu Bal Arg Ser Leu Gln Thr Phe Ser Gln
```

```
        50                  60                  70                  80                  90
        -                   -                   -                   -                   -
ATG     AAA CTC             CCC TTA             CTT CTG             GCT CTT             CTA TTT GGG GCA GTT
MET     Lys Leu             Pro Leu             Leu Leu             Ala Leu             Leu Phe Gly Ala Val 140                 150                 160                 170                 180
        -                   -                   -                   -                   -
GGT GCT AAG                 ACG CTG             CCT GAG             GAT GAG             ACA CCA GAG CAG
Gly Ala Lys                 Thr Leu             Pro Glu             Asp Glu             Thr Pro Glu Gln 230                 240                 250                 260                 270
        -                   -                   -                   -                   -
GGC TCT GGA                 AGT GAA             GAT GCC             TCC AAG             AAA GAT GGG GCT GTT
Gly Ser Gly                 Ser Glu             Asp Ala             Ser Lys             Lys Asp Gly Ala Val 320                 330                 340                 350                 360
        -                   -                   -                   -                   -
GAG GAA GAG                 GAC ACA             GTA AAA             GTG GTG             GGC ATC CCT GGG TGC
Glu Glu Glu                 Asp Thr             Val Lys             Val Val             Gly Ile Pro Gly Cys 410                 420                 430                 440                 450
        -                   -                   -                   -                   -
GCT TGG TTT                 ACT TGC             CGG AGG             TGC TAC             AGG GGC AAC CTG GTT
Ala Trp Phe                 Thr Cys             Arg Arg             Cys Tyr             Arg Gly Asn Leu Val
```

FROM FIG. 16A

FROM FIG. 16A

TO FIG. 16D

```
       460                 470                 480                 490
        |                   |                   |                   |
TCC ATC CAC AAC TTC AAT ATT AAT TAT CGA ATC CAG TGT TCT GTC AGC
Ser Ile His Asn Phe Asn Ile Asn Tyr Arg Ile Gln Cys Ser Val Ser 550                 560                 570                 580
        |                   |                   |                   |
GGC TCG GGT CGC TGC AGA CGC TTT CAG TGG GTT GAC GGC AGC CGC TGG
Gly Ser Gly Arg Cys Arg Arg Phe Gln Trp Val Asp Gly Ser Arg Trp 640                 650                 660                 670
        |                   |                   |                   |
TCA CTG CGT GGC CCT GTG TAC CCG AGG AGG CTA CTG GCG TCG AGC CAC
Ser Leu Arg Gly Pro Val Tyr Pro Arg Arg Leu Leu Ala Ser Ser His 730                 740                 750                 760
        |                   |                   |                   |
CCC AGC CGA CAG TTC AGA GCT GCC CTC TCC TGG GCA TGG CCT CCC CTC 820                 830                 840
        |                   |                   |
GGT TTT ACT GAA AAA AAA AAA AAA AAA AAA AAA AAA AAA AA
```

FIG. 16D

FROM FIG. 16B

```
500         510         520         530         540
 -           -           -           -           -
GCG CTC AAC CAG GGT CAA GTC TGG ATT GGA GGC AGG ATC ACA
Ala Leu Asn Gln Gly Gln Val Trp Ile Gly Gly Arg Ile Thr 590         600         610         620         630
 -           -           -           -           -
AAC TTT GCG TAC TGG GCT GCT CAC CAG CTG GTC CCG CGG TGG
Asn Phe Ala Tyr Trp Ala Ala His Gln Leu Val Pro Arg Trp 680         690         700         710         720
 -           -           -           -           -
TGC CTC AGA AGA CTT CCT TTC ATC TGT TCC TAC TGA GCT GGT
Cys Leu Arg Arg Leu Pro Phe Ile Cys Ser Tyr 770         780         790         800         810
 -           -           -           -           -
CTC TGC TTG CCA TCC CTC CCT CCA CCT CCC TGC AAT AAA ATG
```

FROM FIG. 16C

ANTIMICROBIAL PROTEINS, COMPOSITIONS CONTAINING SAME AND USES THEREOF

This application is a continuation of U.S. Ser. No. 07/677,371, filed Mar. 26, 1991, now abandoned which is a continuation in part of U.S. Ser. No. 276,136, filed Nov. 25, 1988, now abandoned which is a continuation in part of U.S. Ser. No. 125,684, filed Nov. 25, 1987, now U.S. Pat. No. 5,087,569 which is a continuation in part of U.S. Ser. No. 106,524, filed Oct. 6, 1987, now U.S. Pat. No. 5,126,257, issued Jun. 30, 1992, which is a continuation in part of U.S. Ser. No. 935,509, filed Nov. 26, 1986, abandoned, the contents of both of which are hereby incorporated by reference into the subject application.

This invention was made with government support under grant numbers CA 22090 and CA 43610 from the National Cancer Institute and grant numbers AI 07012 and AI 20516 from the U.S. Public Health Seaice. The U.S. Government has certain rights in the invention.

BACKGROUD OF THE INVENTION

Within this application several publications are referenced by Arabic numerals within parentheses. Full citations for these references may be found at the end of the specification immediately preceding the claims. The disclosures of these publications in their entirety are hereby incorporated by reference into this application in order to more fully describe the state of the art to which this invention pertains.

One of the major roles of granulocytes in the blood is defense of the host against bacterial, fungal and parasitic infection. Neutrophils are believed to have the major role in bacterial and fungal killing while eosinophils are thought to play the key role in parasitic killing. Two distinct systems of microbial killing are recognized in the neutrophil (1). In the oxygen-dependent system, neutrophil enzymes NADPH oxidase, superoxide dismutase and myeloperoxidase participate in a complex series of reactions which result in generation of oxygen metabolites capable of microbial killing. A second neutrophil system consists of granule proteins which exhibit direct oxygen-independent antimicrobial activity.

A number of proteins packaged in the neutrophil azurophil granule have demonstrated antimicrobial activity in vitro including bactericidal/permeability increasing factor (2), lysozyme (3), cathepsin G (4), elastase (5) and defensin (6). Although purified preparations of these proteins kill in vitro, microbicidal activity of the neutrophil in vivo is probably the result of interaction of these proteins and elements of the oxygen-dependent pathways. The proteins involved in microbial killing act by a number of different mechanisms, both enzymatic and non-enzymatic, which may indicate that a different subset of the available proteins may be active depending on the target organism. No systematic study of the relative contributions of these proteins to the killing of various target organisms has been reported, however.

Eosinophil-mediated killing of parasites resembles neutrophil-mediated killing of bacteria and fungus in several ways. Eosinophils also have granules containing proteins which are involved in killing target organisms. One of these proteins is eosinophil peroxidase, which can participate in oxygen-dependent mechanisms of killing (7). The granules also contain at least two proteins, eosinophil cationic protein (ECP) and eosinophil major basic protein, which can directly kill eosinophil target organisms. Eosinophil major basic protein is the major protein of the eosinophil granule, constituting perhaps 70% of the granule protein content (8). The primary structure of MBP has been established by protein sequencing (9) and more recently by cDNA cloning (10) and indicates a molecular weight of 13800 and a pI greater than 10. Although the mechanism of action of MBP has not been established it is thought that the high positive charge and hydrophobicity of the protein promotes strong disruptive interactions with membranes.

Eosinophil cationic protein is another major constituent of eosinophil granules, estimated as 20% of granule protein (8). Multiple forms of ECP are found by sodium dodecyl sulfate-polyacrylamide gel analysis of granule proteins. These apparently arise due to glycosylation differences, since deglycosylation using Endoglycosidase F eliminates the observed heterogeneity (11). The N-terminal amino acid sequence of ECP through 59 residues has been reported and bears significant homology to human pancreatic ribonuclease (11). ECP is able to form pores in both synthetic lipid membranes and in the membranes of a number of cell types (12) and may represent the mechanism by which ECP damages parasite targets. Although both MBP and ECP are toxic to parasites such as Shistosomula mansons (13), no antibacterial activity has been reported for ECP or MBP (8, 14, 15).

SUMMARY OF THE INVENTION

The present invention provides a purified polypeptide useful as an antimicrobial agent. This polypeptide comprises a human polymorphonuclear leukocyte polypeptide having a molecular weight of about 25,000 daltons and the amino acid sequence shown in FIG. 16, or a fragment derived therefrom.

Further provided is a purified polypeptide useful as an antimicrobial agent which comprises a human polymorphonuclear leukocyte polypeptide having an apparent molecular weight of about 54,000 daltons. The polypeptide has respiratory burst-independent, antibacterial activity at a pH from about 5.0 to about 8.0, at calcium ion concentrations up to about 10 mM, and at sodium chloride concentrations up to about 0.3M.

Also provided is a purified polypeptide useful as an antimicrobial agent which comprises a human polymorphonuclear leukocyte polypeptide having an apparent molecular weight of about 29,000 daltons, respiratory burst-independent, antimicrobial activity against bacteria and fungi at a pH from about 5.0 to about 8.0 and at calcium ion concentrations up to about 10 mM, bactericidal activity at sodium chloride concentrations up to about 0.3M, and fungicidal activity at sodium chloride concentrations up to about 0.15M.

BRIEF DESCRIPTION OF THE FIGURES

FIG. 1B Profile of bactericidal activity. Each fraction was extracted with 0.05M glycine-HCl pH 2.0, centrifuged at 10,000×g for 20 minutes and the supernatant incubated with E. coli K12, at a protein concentration of 5 micrograms/ml. The percentage of bacteria killed after 30 minutes incubation at 37° C. is presented here. Inset (C) shows the amount of protein from purified azurophils (●) and purified specific granules (Δ) necessary to produce 50% reduction in bacterial colony-forming units ($LD_{50}$).

Isolated azurophil granules in relaxation buffer (pH 7.3, see Materials and Methods) were disrupted by freeze-thaw/sonication and centrifuged. The supernatant (■), the pelleted material (●) and the total granules (Δ) were extracted at pH 2.0 and tested for bactericidal activity.

Figure 3:
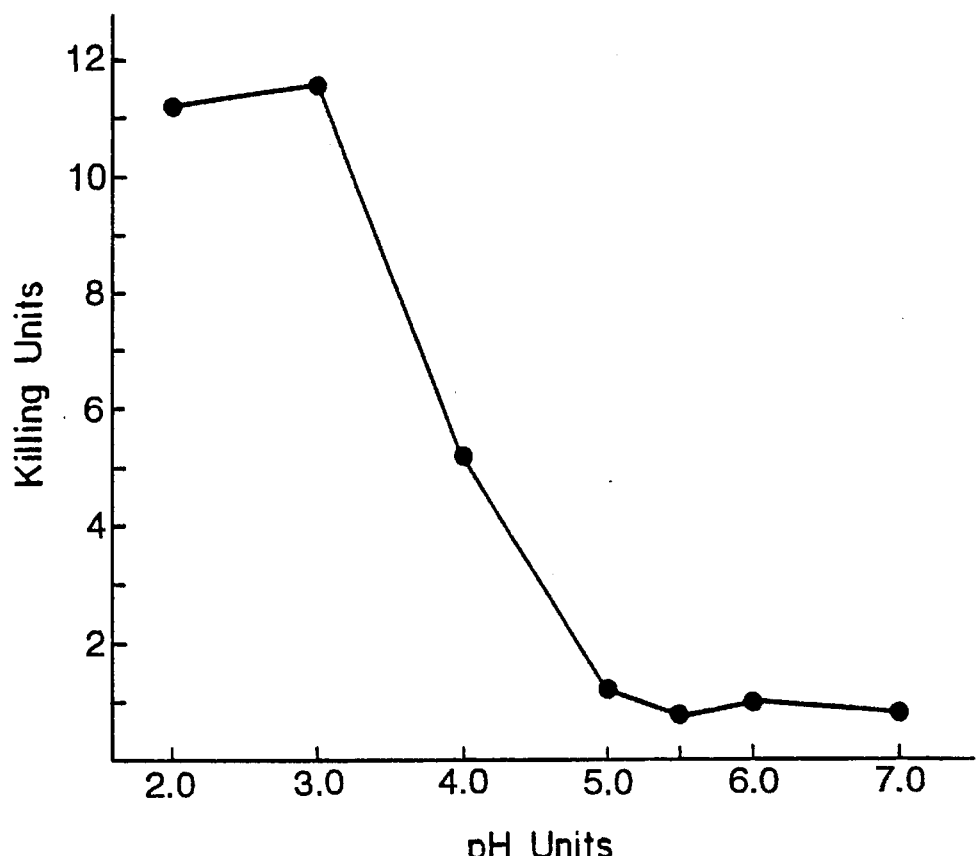

FIG. 3. Effect of pH on the extraction of a bactericidal factor from azurophil granule membranes Aliquots of azurophil membranes were added to various buffer systems (0.05M): glycine, pH 2.0–3.0; citrate, pH 4.0–6.0; phosphate, pH 7.0. After incubation at 25° C. for 40 minutes, the suspensions were centrifuged at 10,000×g for 20 minutes and the supernatants assayed for protein content and bactericidal activity. Killing units (K.U.) correspond to the reciprocal of the number of micrograms/ml of protein necessary to kill 105 bacteria in 30 minutes at 37° C. In each case, the bactericidal assay was conducted in 0.05M citrate buffer, pH 5.5.

Figure 4:
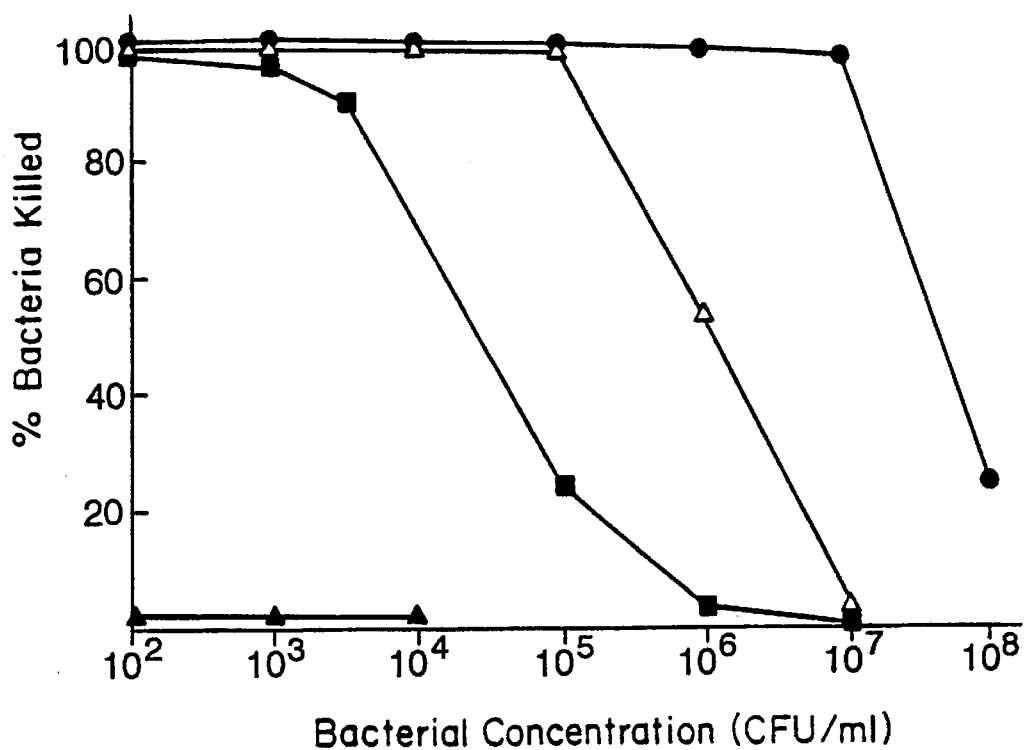

FIG. 4. Bactericidal activity of azurophil granule extract on increasing concentrations of bacteria Granule extract was prepared as described in Materials and Methods. 30 micrograms/ml (●), 3 micrograms/ml (Δ), 0.3 micrograms/ml (■), or 0.03 micrograms/ml (▲) of the azurophil extract were added for each bacterial concentration tested.

Figure 5:
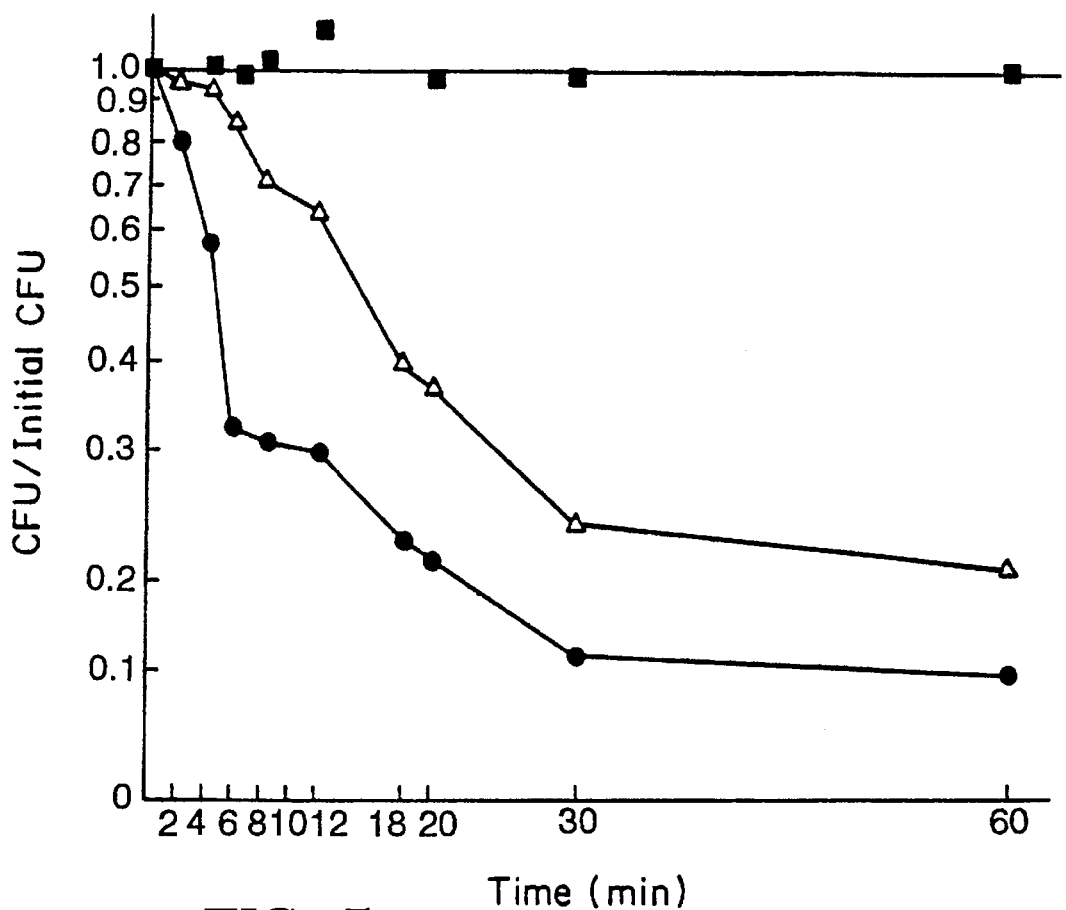

FIG. 5. Kinetics of bactericidal activity of an azurophil-derived bactericidal factor E. coli K12 cells ($2 \times 10^5$ CFU/ml) were incubated with 1.4 micrograms/ml (●) or 0.7 micrograms/ml (Δ) of azurophil granule extract in 0.05M citrate buffer pH 5.5 and with citrate buffer alone (■).

Figure 6:
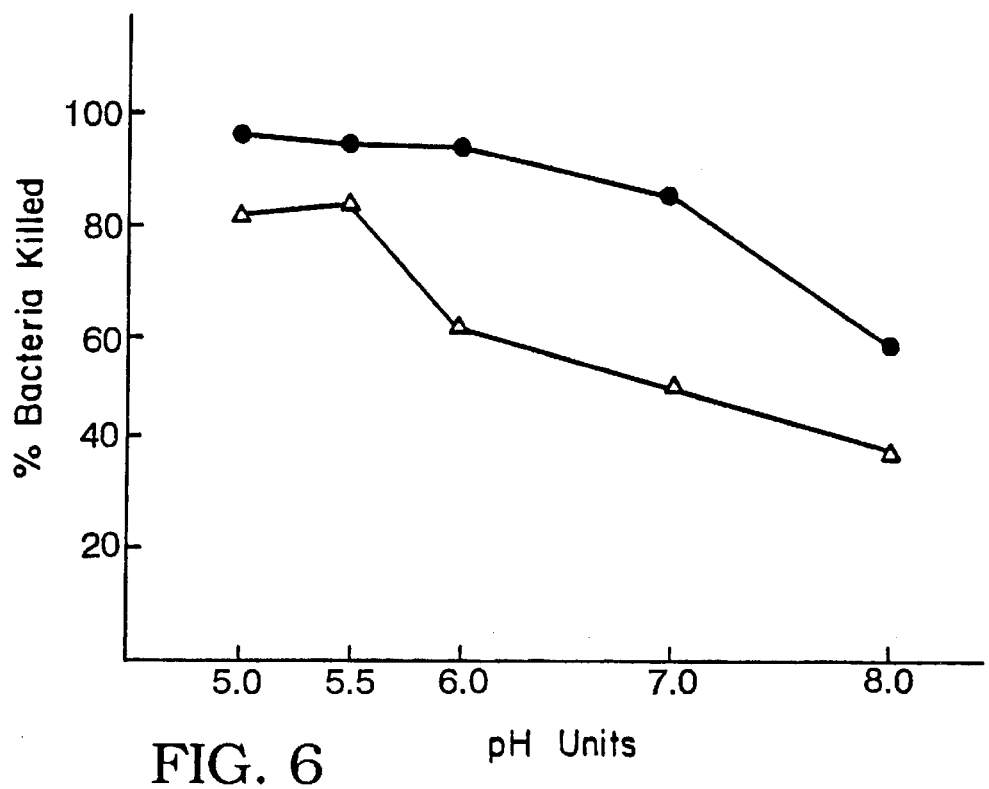

FIG. 6. Effect of pH on bactericidal activity of an azurophil-derived bactericidal factor E. coli K12 cells ($2.5 \times 10^5$ CFU/ml) were incubated for 30 minutes at 37° C. with 2.8 micrograms/ml (●) or 0.7 micrograms/ml (Δ) of azurophil granule extract in citrate buffer pH 5 and 5.5 and sodium phosphate or sodium phosphate-citrate buffer pH 6.0 to 8.0.

Figure 7:
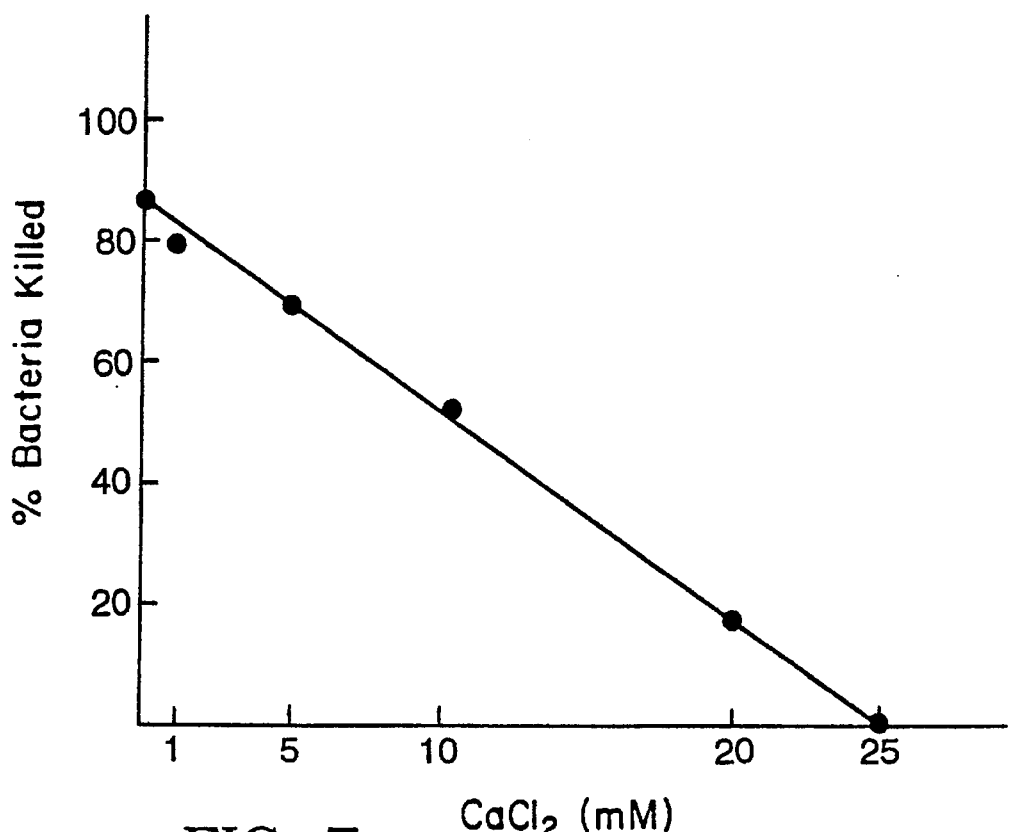

FIG. 7. Effect of $Ca^{2+}$ ions on bactericidal activity of an azurophil-derived bactericidal factor E. coli K12 cells ($2.5 \times 10^5$ CFU/ml) were incubated for 30 minutes at 37° C. with 2.8 micrograms/ml of azurophil granule extract in 0.05M citrate buffer 5.5, supplemented with $CaCl_2$ as shown.

Figure 8:
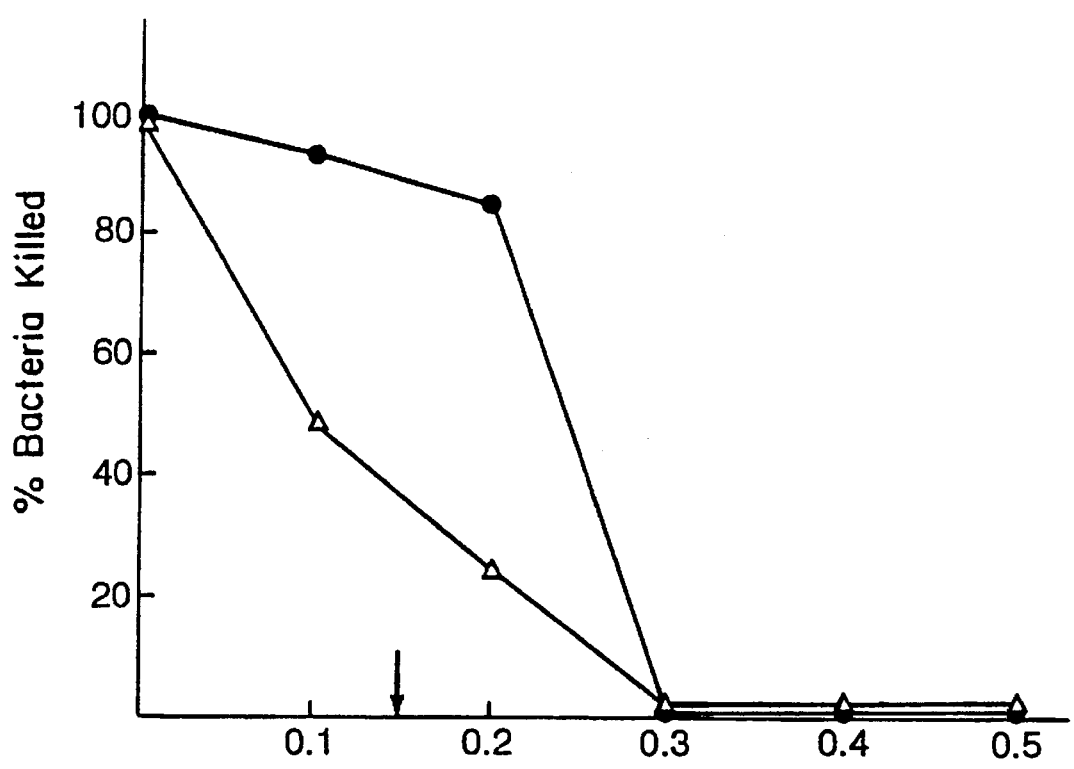

FIG. 8. Effect of sodium chloride concentration on bactericidal activity of an azurophil-derived bactericidal factor E. coli K12 cells ($2.5 \times 10^5$ CFU/ml) were incubated for 30 minutes at 37° C. with 2.8 micrograms/ml (●) or 1.4 micrograms/ml (Δ) of azurophil-granule extract in 0.05M citrate buffer pH 5.5, supplemented with NaCl as shown. Arrow indicates NaCl concentration of plasma.

Figure 9:
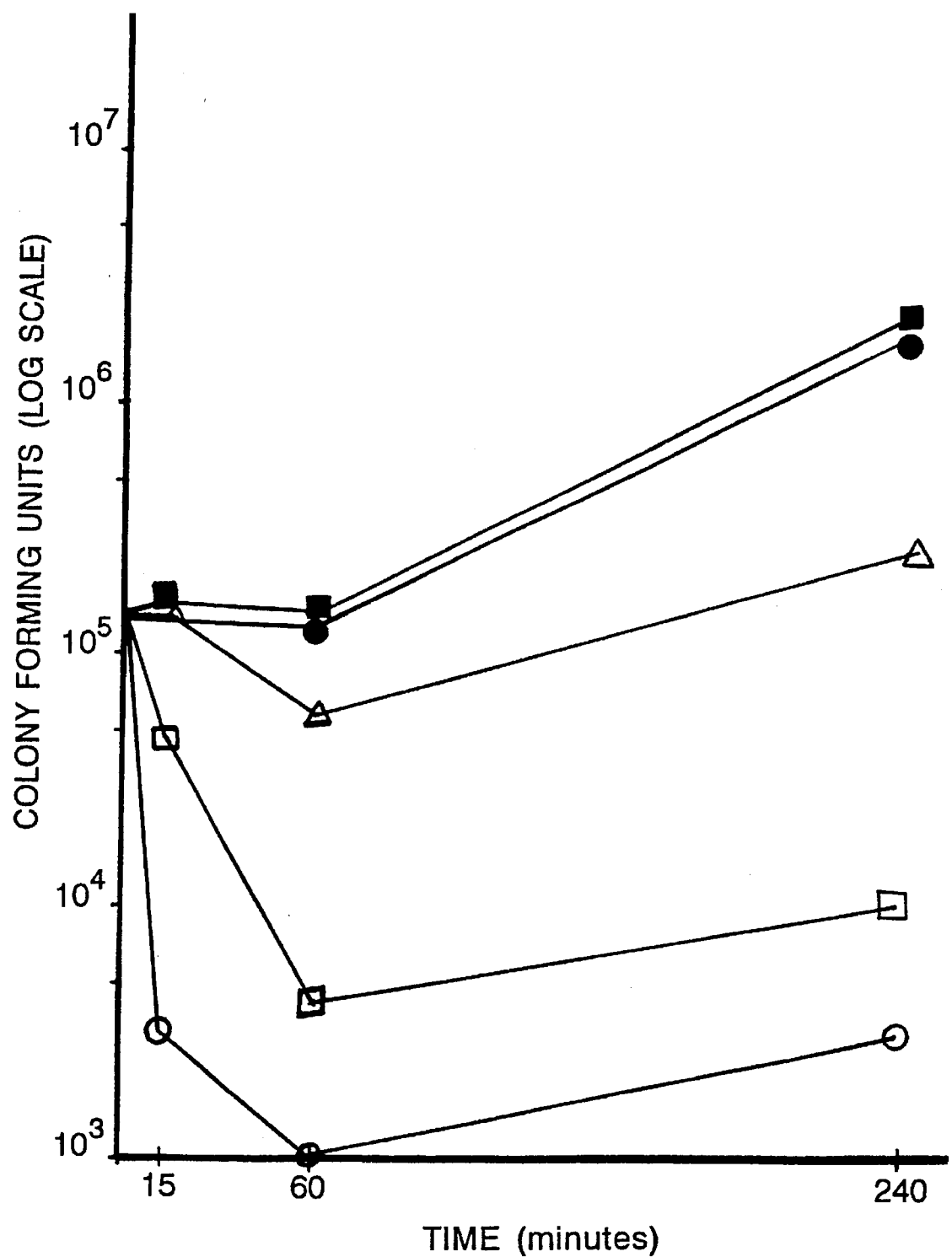
Figure 10A:
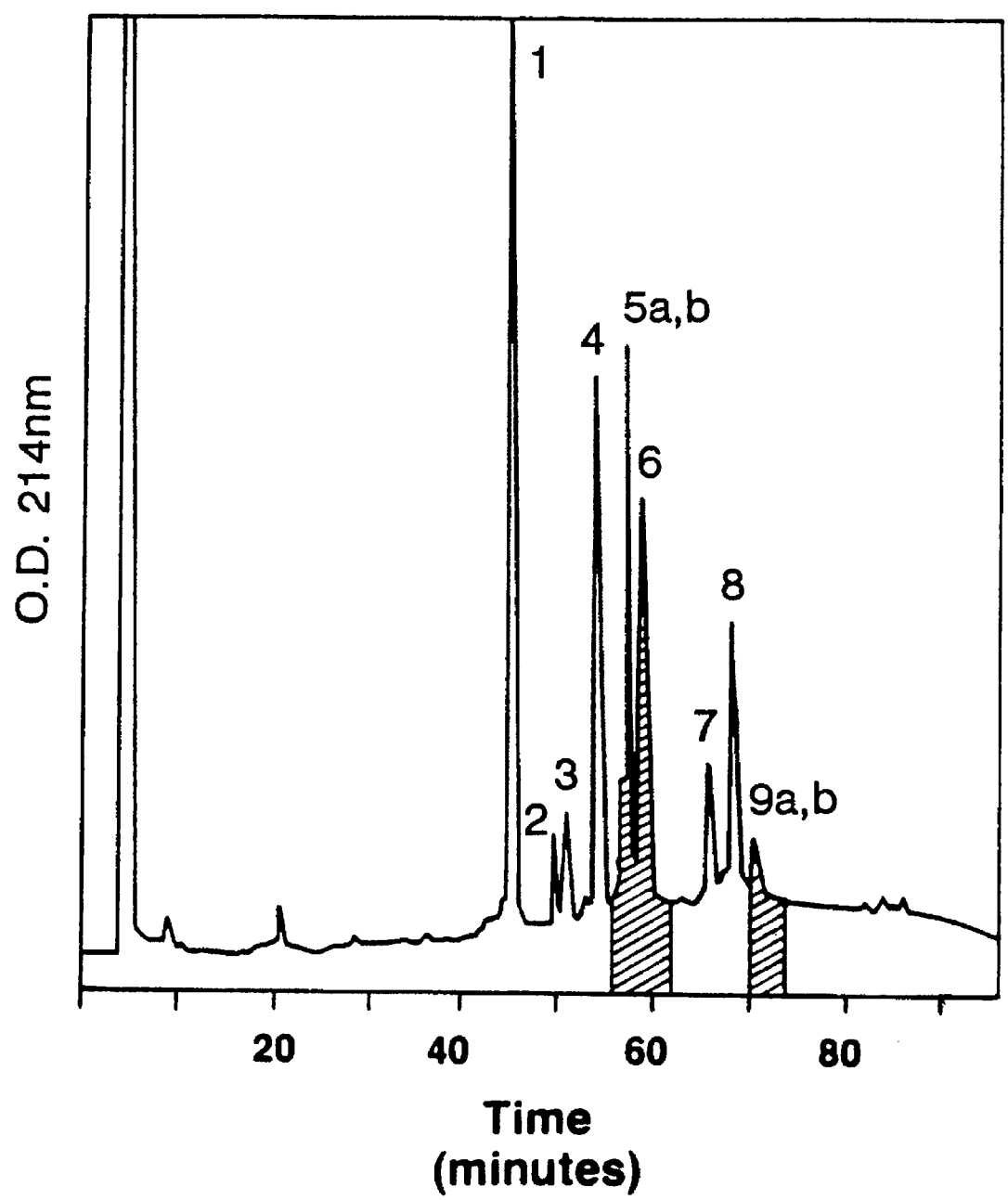
Figure 10B:
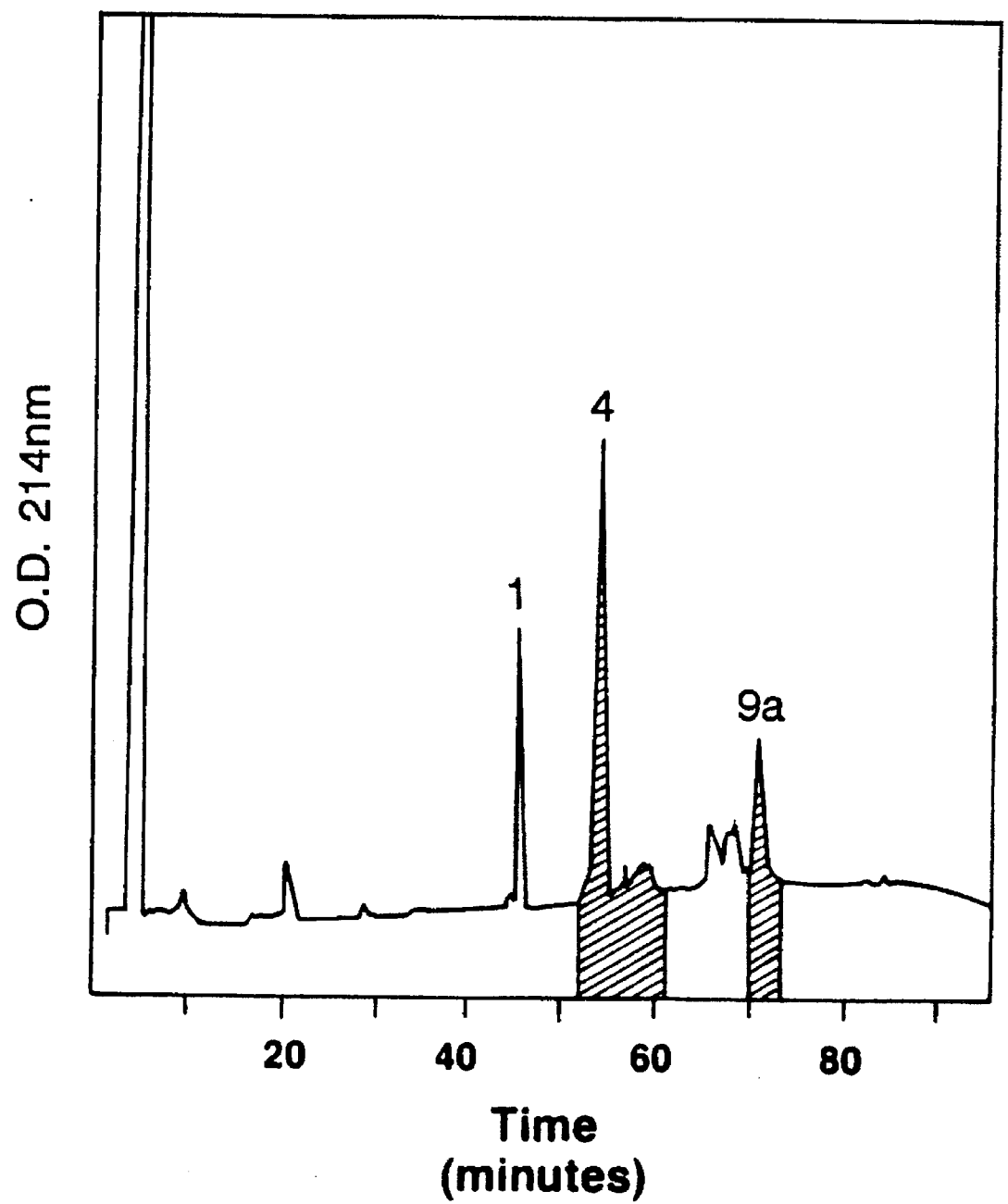
Figure 10C:
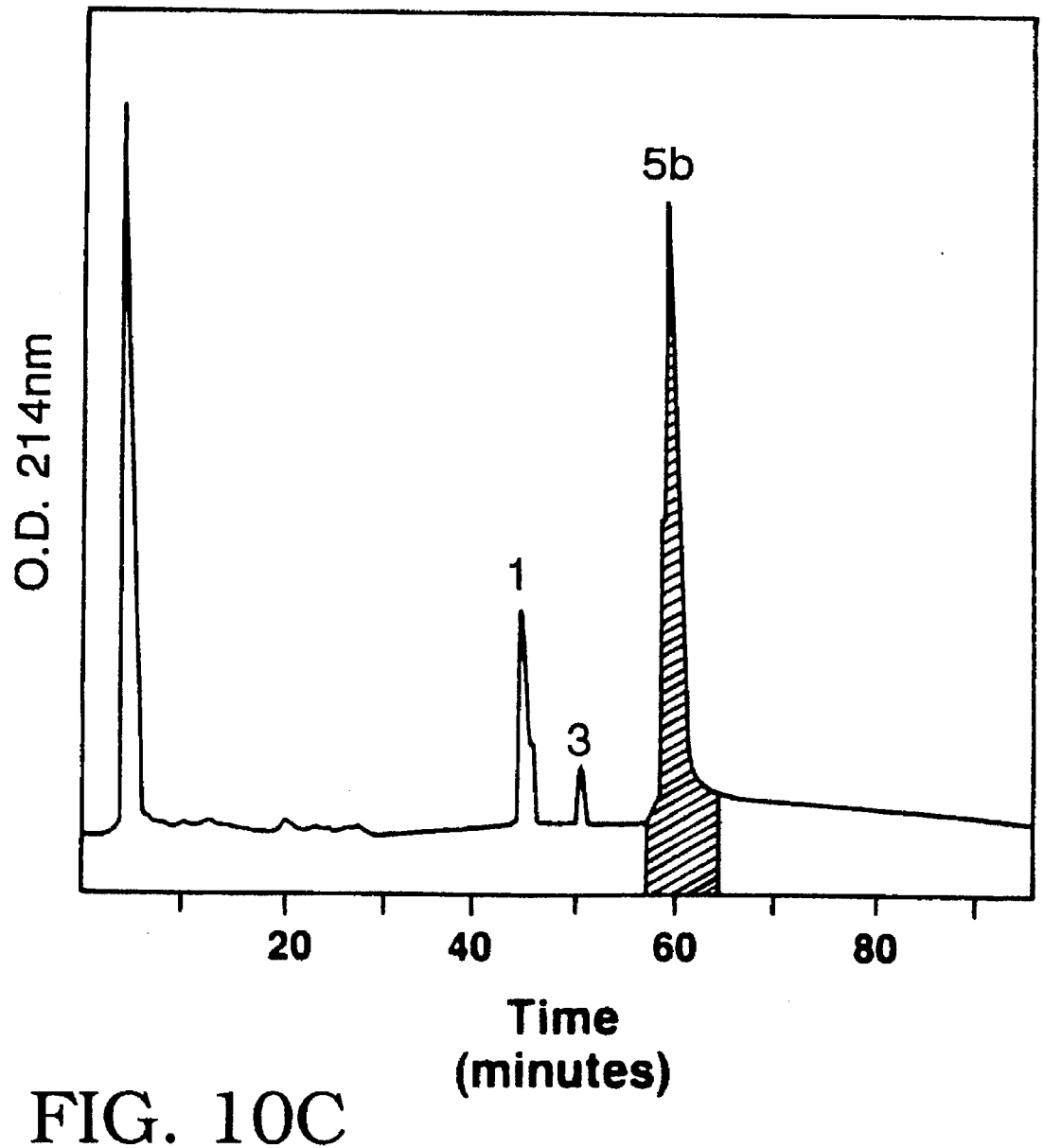

FIG. 9. Fungicidal activity of ABDF at various times and concentrations was measured:

(■)=1.6 micrograms ADBF/ml
(Δ)=3.2 micrograms ADBF/ml
(☐)=8 micrograms ADBF/ml
(o)=16 micrograms ADBF/ml
(●)=control FIGS. 10A, 10B, and 10C Reverse phase high performance liquid chromatography of ADBF Reverse phase high performance liquid chromatography was carried out as described in materials and methods. The column was monitored at 214 nm (0.5 AUFS) and 1 ml fractions collected. For assay, 100 microliters of each fraction was dried in a Savant Speed-Vac®, resuspended in 100 microliters of 0.1% acetic acid, redried and finally resuspended in 160 microliters of 0.05M citrate pH 5.5. Forty microliters of E. coli K12 were added to give $2 \times 10^5$ CFU/ml final concentration and incubated at 37° C. for 30 minutes. The crosshatched areas indicate regions of 100% killing. Panel A represents crude ADBF: FIG. 10B, TSK purified ADBF (50–60 kD peak); and FIG. 10C TSK purified ADBF (10–20 kD peak).

FIG. 11. N-terminal sequence analysis of azurophil-derived proteins purified by reverse phase high performance liquid chromatography (single-letter designation) (Seq ID No. 11–22 for peaks 1, 2, 3, 4, 5a, 5b, 6, 7, 8a, 8b, 9a, and 9b, respectively)

Shown is the cumulative sequence data (from several analyses) corresponding to each of the major reverse phase peaks shown in FIG. 10.
Peak 1=defensin; Peak 4=cathepsin G;
Peak 5a=lysozyme; and Peak 8=elastase.

Figure 12:
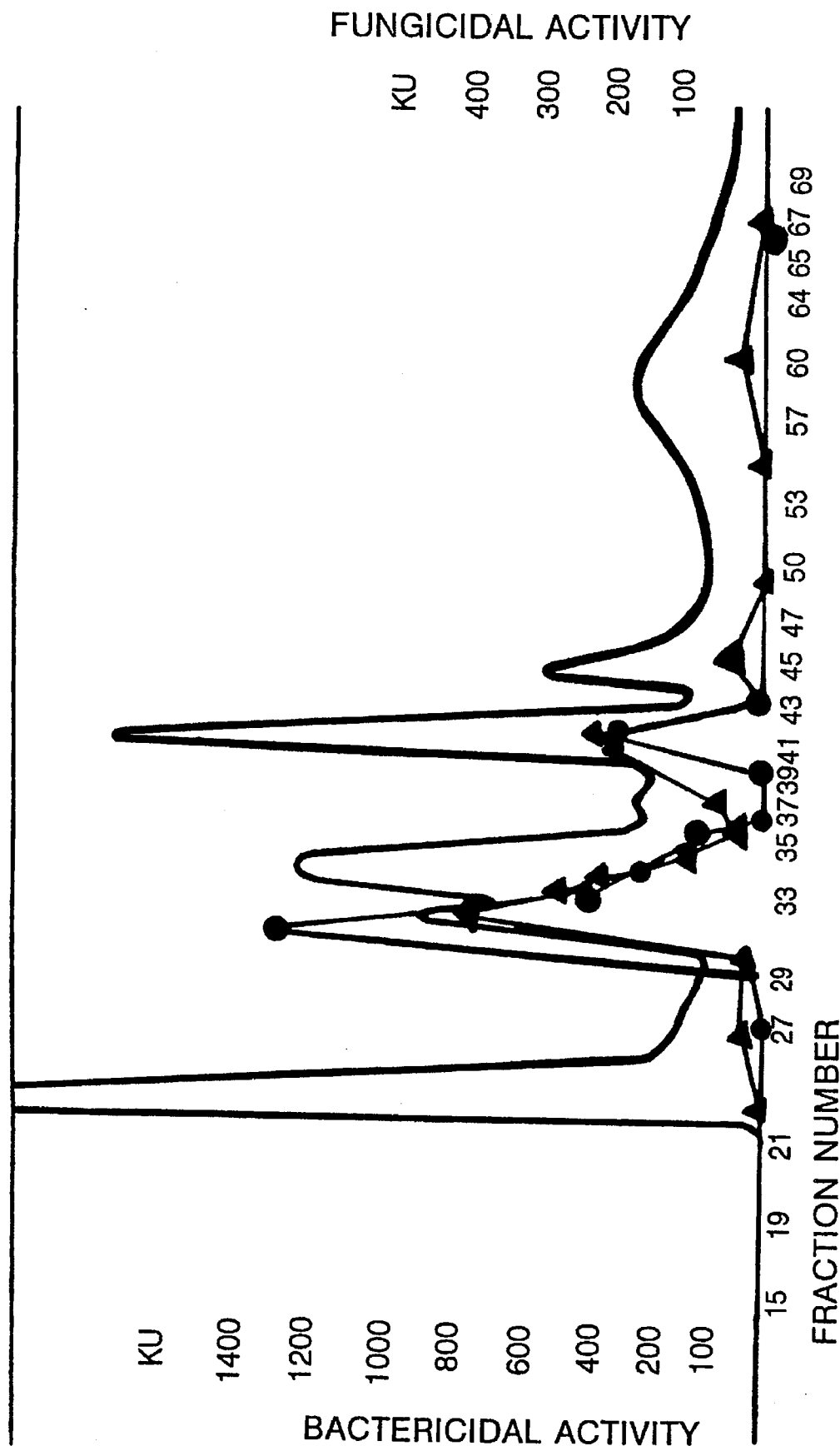

FIG. 12. ADBF size exclusion chromatogram 1 mg of ADBF was run on a TSK size exclusion column as described herein.
(●)=bactericidal activity profile.
(▲)–fungicidal activity profile.
(–)=UV profile.

Figure 13:
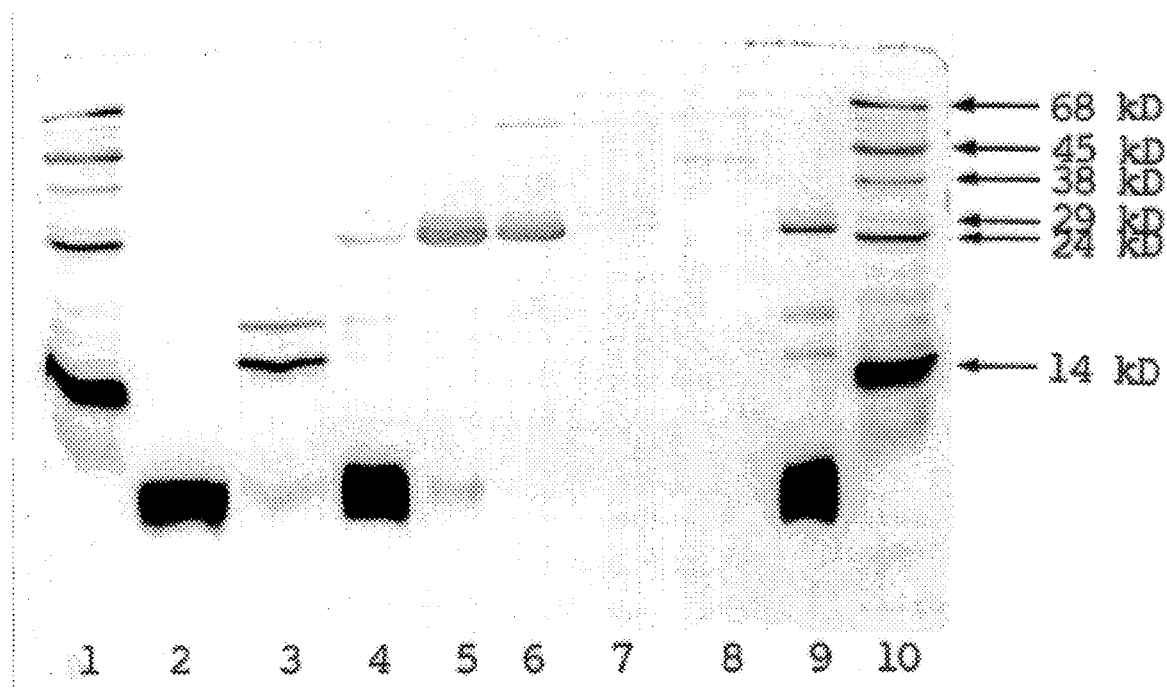

FIG. 13. SDS-PAGE of ADBF and fractions obtained from TSK size exclusion chromatography ADBF and various ADBF fractions from the chromatograph shown in FIG. 12 were collected and run under reducing conditions on a 15% SDS polyacrylamide gel. Lanes 1 and 10=low molecular weight markers; lane 2=fraction 58; lane 3=fraction 41; lane 4=fraction 34; lane 5=fraction 33; lane 6=fraction 32; lane 7=fraction 31; lane 8=fraction 30; and lane 9=ADBF prior to size exclusion chromatography.

Figure 14:
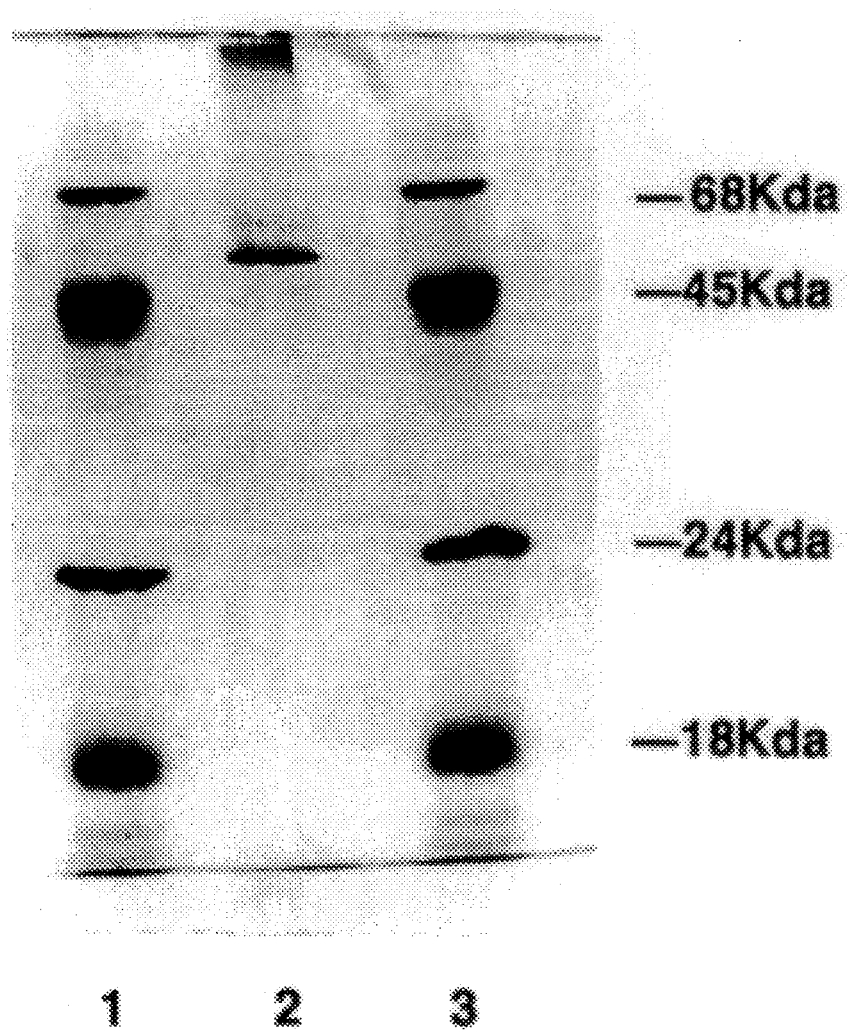

FIG. 14. SDS-PAGE of TSK—RPHPLC peak 9

Peak 9 from RPHPLC (FIG. 13) was loaded on a reducing 10%. SDS polyacrylamide gel.
Lanes 1 and 3=molecular weights markers; lane 2=peak 9

Figure 15:
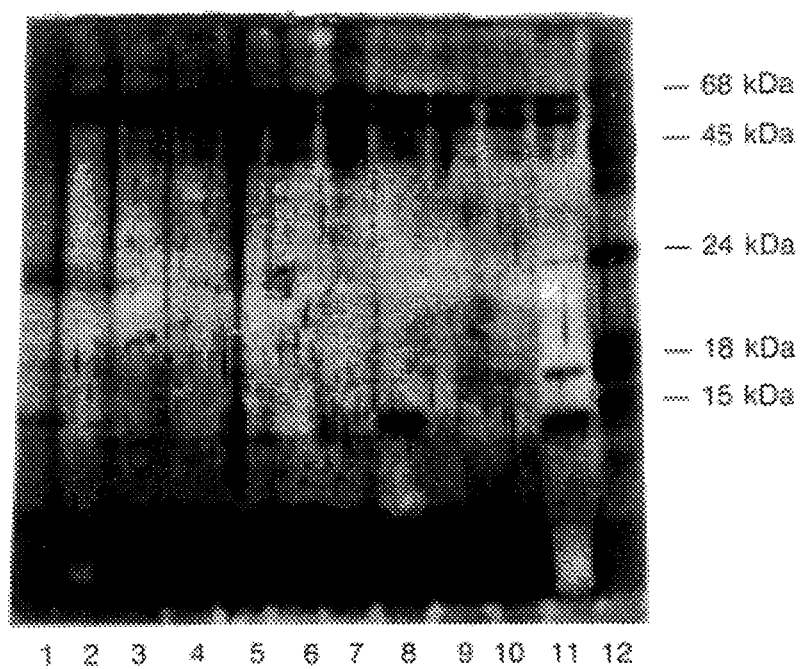

FIG. 15. SDS-PAGE of TSK-RPHPLC peak 5b

Consecutive fractions from RPHPLC corresponding to elution times from 45–65 minutes were run on a 12% SDS polyacrylamide gel.
Lane 8 contains peak 5b (from FIG. 10C) and lane 11 contains the starting material, which consisted of TSK peak fraction 42.

FIGS. 16A–D cDNA-protein sequences of 25,000 dalton/13,000 dalton ADBF polypeptides (SEQ ID NO:23)

Figure 17:
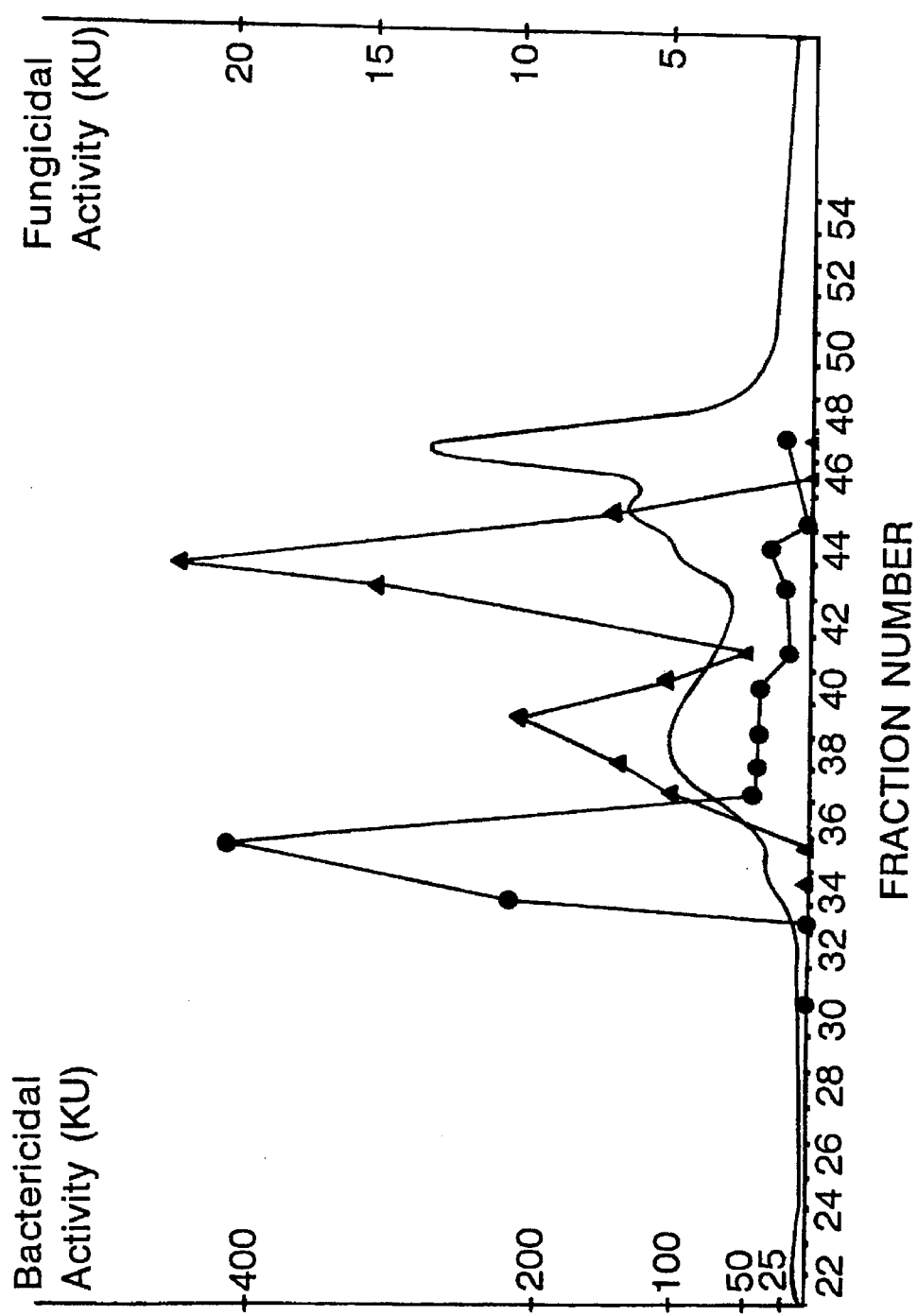

FIG. 17. ADBF size exclusion chromatography in high salt

ADBF was run on TSK size exclusion chromatography in 50 mM glycine pH 2, 500 mM NaCl.
(●)=bacterial activity profile
(▲)=fungicidal activity profile
(–)=$UV_{280}$ profile FIG. 18. SDS-PAGE of fractions obtained from TSK size exclusion chromatography in high salt Various ADBF fractions obtained from the chromatogram shown in FIG. 17.

Lanes 1 and 3=ADBF extract; lanes 2 and 12=molecular weight markers; lanes 4 and 5=fractions 34 and 35, respectively (p54); lane 6=fraction 36; lanes 7,8, and 9=fractions 37,38, and 39, respectively (p29); lane 10=fraction 43 (p14 chiefly); lane 11=fraction 45 (p18+ p14).

DETAILED DESCRIPTION OF THE INVENTION

The present invention provides a purified polypeptide useful as an antimicrobial agent. This polypeptide comprises a human polymorphonuclear leukocyte polypeptide having a molecular weight of about 25,000 daltons and the amino acid sequence shown in FIG. 16, or a fragment derived therefrom. A DNA molecule encoding this polypeptide is also provided which comprises the nucleotide sequence shown in FIGS. 16A–D.

Within the context of the present invention, it is understood that variations in proteins and nucleic acids exist among individuals, e.g. amino acid or nucleotide substitutions, deletions, insertions, and degree or location of glycosylation, and that functional derivatives resulting therefrom are included within the scope of the present invention.

In one embodiment of the invention the purified polypeptide has an apparent molecular weight of about 13,000 daltons. In a preferred embodiment of the invention the polypeptide has a predicted molecular weight of about 13,000 daltons. This polypeptide may comprise the amino acid sequence shown in FIGS. 16A–D from amino acid 106 to amino acid 221. A DNA molecule encoding this polypeptide is provided. In one embodiment, the DNA molecule comprises the DNA molecule comprises the DNA sequence shown in FIGS. 16A–D from nucleotide 364 to nucleotide 709. In still another embodiment of the invention, the polypeptide has an apparent molecular weight of about 18,000 daltons. A DNA molecule encoding this polypeptide is further provided.

A method for killing a microorganism, e.g. a bacteria, fungus, or virus, is also provided. This method comprises contacting the microorganism with an effective microorganism killing amount of the polypeptide having a molecular weight of about 25,000 daltons, or a fragment thereof, provided by the present invention.

A vector which comprises the DNA molecule encoding the polypeptide of the present invention having a molecular weight of about 25,000 daltons, or a fragment thereof, is also provided. In one embodiment of the invention the vector comprises a plasmid. Moreover, a host vector system for the production of the 25,000 dalton polypeptide, or a fragment thereof, is provided which comprises a plasmid of the present invention in a suitable host. This host vector system may be grown under suitable conditions which permit the production of the 25,000 dalton polypeptide of the present invention, or a fragment thereof, and the resulting polypeptide may be recovered.

A method is also provided for preparing the purified 25,000 dalton polypeptide, or fragment thereof, which comprises culturing neutrophil precursor cells, harvesting the cells and suspending them in a suitable buffer. The resulting neutrophil precursor cell suspension is treated so as to obtain a suspension of lysed neutrophil precursor cells, and the suspension is separated so as to obtain a nuclei and unbroken cell phase and a post nuclear supernatant. The postnuclear supernatant is recovered and treated with an extracting reagent having a pH less than about 8.0 and capable of solubilizing membrane proteins so as to obtain an extracting reagent phase and an insoluble membrane phase. The extracting reagent phase is separated from the insoluble membrane phase so as to obtain a soluble protein phase and an insoluble membrane phase. The soluble protein phase is recovered and purified so as to obtain the 25,000 dalton polypeptide of the present invention, or fragment thereof.

In one embodiment of the invention, the neutrophil precursor cells are HL60 cells. In another embodiment of the invention, prior to treating the neutrophil precursor cell suspension so as to obtain a suspension of lysed neutrophils, the suspension is treated with a suitable protease inhibitor. In another embodiment of the invention, prior to separating the suspension of lysed neutrophils, the suspension is treated with a suitable chelating agent.

In yet another embodiment of the invention, the soluble protein phase is purified by ion exchange chromatography. Moreover, the soluble protein phase may be purified by size exclusion chromatography, affinity chromatography or immuno-affinity chromatography.

The present invention also provides a pharmaceutical composition which comprises the 25,000 dalton polypeptide, or fragment thereof, provided herein and a pharmaceutically acceptable carrier. This pharmaceutical composition may be used to treat a subject having a bacterial or fungal infection by administering to the subject an effective bacterial or fungal killing amount of the pharmaceutical composition.

A method for killing a microorganism is also provided. This method comprises contacting the microorganism with an effective microorganism killing amount of the 18,000 dalton polypeptide of the present invention.

The present invention also provides a pharmaceutical composition which comprises the 18,000 dalton polypeptide provided herein and a pharmaceutically acceptable carrier. This pharmaceutical composition may be used to treat a subject having a microorganism infection by administering to the subject an effective microorganism killing amount of the pharmaceutical composition.

The present invention further provides yet another a purified polypeptide useful as an antimicrobial agent which comprises a human polymorphonuclear leukocyte polypeptide having an apparent molecular weight of about 54,000 daltons. This polypeptide has respiratory burst-independent, antibacterial activity at a pH from about 5.0 to about 8.0, at calcium ion concentrations up to about 10 mM, and at sodium chloride concentrations up to about 0.3M. In one embodiment of the invention the polypeptide additionally has antifungal activity at a pH from about 5.0 to about 8.0, at calcium ion concentrations up to about 10 mM, and at sodium chloride concentrations up to about 0.15M.

In another embodiment of the invention, the polypeptide comprises the N-terminal amino acid sequence Val-Asn-Pro-Gly-Val-Val-Val-Arg-Ile-Ser-Gln-Lys-Gly-Leu-Asp-Tyr-Ala-Ser-Gln-Gln-Gly-Thr-Ala-Ala-Leu-Gln-X-X-Leu-Lys-His-Ile-Lys-Ile-Pro-Asp-Tyr-Leu. (SEQ ID NO:1).

A method for killing bacteria or fungi is also provided. This method comprises contacting the bacteria or fungi with an effective bacterial or fungal killing amount of the 54,000 dalton polypeptide of the present invention.

Further provided is a DNA molecule which encodes the 54,000 dalton polypeptide of the present invention and a vector which comprises the DNA molecule The present invention also provides a vector which comprises the plasmid of the present invention. Moreover, a host vector system for the production of the 54,000 dalton polypeptide of the present invention is provided which comprises a plasmid of the present invention in a suitable host. This host vector system may be grown under suitable conditions which permit the production of the 54,000 polypeptide of the present invention and the resulting polypeptide may be recovered.

The present invention also provides a pharmaceutical composition which comprises the 54,000 dalton polypeptide provided herein and a pharmaceutically acceptable carrier. This pharmaceutical composition may be used to treat a subject having a bacterial infection by administering to the subject an effective bacterial killing amount of the pharmaceutical composition. In another embodiment of the invention the pharmaceutical composition may be used to treat a subject having a bacterial or fungal infection by administering to the subject an effective bacterial or fungal killing amount of the pharmaceutical composition.

The present invention further provides another purified polypeptide useful as an antimicrobial agent. This polypeptide comprises a human polymorphonuclear leukocyte polypeptide having an apparent molecular weight of about 29,000 daltons.

In one embodiment of the invention the polypeptide is derived from the azurophil granule extract fraction corresponding to peak 6 in FIG. 10A. In another embodiment the purified polypeptide which comprises the N-terminal amino acid sequence Ile-Val-Gly-Gly-Arg-Lys-Ala-Arg-Pro-Arg-Gln-Phe-Pro-Phe-Leu-Ala-Ser-Ile-Gln-Asn-Gln-Gly-Arg-His-Phe (SEQ ID NO:2). In still another embodiment of the invention the polypeptide is derived from the azurophil granule extract fraction corresponding to peak 7 in FIG. 10A. In yet a further embodiment the purified polypeptide comprises the N-terminal amino acid sequence Ile-Val-Gly-Gly-His-Glu-Ala-X-X-Pro-Ser-Asp-Pro-Tyr-Met-Asp-Ser-Leu-Asp-Met (SEQ ID NO:3).

A method for killing bacteria or fungi is also provided. This method comprises contacting the bacteria or fungi with an effective bacterial or fungal killing amount of the 29,000 dalton polypeptide of the present invention.

Further provided is a DNA molecule which encodes the 29,000 dalton polypeptide of the present invention. A vector which comprises the DNA molecule of the present invention is also provided. In one embodiment of the invention the vector comprises a plasmid. Moreover, a host vector system for the production of the 29,000 dalton polypeptide of the present invention is provided which comprises a plasmid of the present invention in a suitable host. This host vector system may be grown under suitable conditions which permit the production of the 29,000 dalton polypeptide of the present invention and the resulting polypeptide may be recovered.

The present invention also provides a pharmaceutical composition which comprises the 29,000 dalton polypeptide provided herein and a pharmaceutically acceptable carrier. This pharmaceutical composition may be used to treat a subject having a bacterial or fungal infection by administering to the subject an effective bacterial or fungal killing amount of the pharmaceutical composition.

The compositions of matter, polypeptides, and methods of the present invention will be better understood by reference to the following experiments and examples, which are provided for purposes of illustration and are not to be construed as in any way limiting the scope of the invention, which is defined by the claims appended.

Materials and Methods
Isolation of neutrophils

Blood obtained from healthy donors was anticoagulated with 25 mM sodium citrate and mixed with an equal volume of 6% dextran in 0.9% NaCl to enhance the sedimentation of erythrocytes. After 60 minutes at room temperature, the leukocyte-rich supernatant was collected and centrifuged at 200×g for 10 minutes. The cell pellets were resuspended in 0.9% NaCl and PMNs were separated from mononuclear cells by centrifugation through Ficoll-Hypaque™. Contaminating erythrocytes were removed by two successive cycles of hypotonic lysis as described (16, 17). More than 98% of the cells were PMNs, of which more than 95% were neutrophils and less than 3% were eosinophils. This preparation was referred to as neutrophils. One unit of blood yielded $10^9$ neutrophils.

Subcellular fractionation of neutrophils

Isolated neutrophils in phosphate-buffered saline ($2\times10^7$ cells/ml) were treated with 5 mM diisopropylfluorophosphate (DFP) for 15 minutes at 4° C. The DFP-treated cells were centrifuged at 130×g for 10 minutes at 4° C., and the resulting pellet was resuspended in an ice-cold buffer containing 100 mM KCl, 3 mM NaCl, 1 mM ATP$(Na)_2$, 3.5 mM $MgCl_2$, and 10 mM Pipes, pH 7.3 (relaxation buffer). The cell suspension was disrupted by nitrogen cavitation for 20 minutes at 350 psi in a bomb (Parr Instrument Company, Moline, Ill.) at 4° C. and the cavitate was collected into the $Ca^{2+}$ ion chelator EGTA, pH 7.4, at a final concentration of 1.5 mM. Nuclei and unbroken cells were pelleted ($P_1$) by centrifugation at 500×g for 10 minutes at 4° C. The post-nuclear supernatant ($S_1$) was centrifuged for 15 minutes at 20,000 rpm (SS 34 rotor) on a discontinuous Percoll™ density grandient, as described (16). Fractions of approximately 1 ml were collected at 4° C. and assayed for specific markers of azurophil granules (β-glucuronidase and myeloperoxidase), specific granules (vitamin B12-binding protein) and plasma membrane (alkaline phosphatase) as described below. Percoll™ was removed from pooled fractions by centrifugation at 35,000 rpm (180,000×g) for 2 hours in an SW41 rotor. The layer that sedimented above the packed Percoll™ was resuspended in relaxation buffer and stored in aliquots at −70° C.

Assays for specific markers in subcellular fractions

To ensure complete solubilization, aliquots of azurophil granules in relaxation buffer were diluted 1:5 in Triton X-100™ (0.05% w/v final concentration) prior to enzyme or protein assays. Alkaline phosphatase was assayed with 1 mg/ml p-nitrophenyl phosphate as substrate in a 0.3 mM $MgCl_2$, 50 mM sodium barbital buffer, pH 10.5. 50 microliter samples diluted in Triton X-100™ were assayed. Samples were incubated for 80 minutes at 37° C. in the assay mixture (1 ml volume) and the reaction was terminated by addition of 100 microliters of 1N NaOH. The absorbance at 410 nm was read immediately. The enzyme activity was calculated as described (18).

β-glucuronidase was assayed by liberation of phenolphthalein from 1 mM phenolphthalein β-monoglucuronic acid in 100 mM sodium acetate buffer, pH 4.4., at 37° C. for 3 hours. 25 microliter samples diluted in Triton X-100™ were assayed in 550 microliters of assay mixture. The reaction was terminated by adding 200 microliters 1M glycine, 1M NaCl, 1M NaOH and the absorbance read at 550 nm. The enzyme activity was calculated as described (16).

Vitamin B12-binding protein was measured on 25-, 50- and 100 microliter samples diluted in Triton X-100™ essentially as described (19). $^{57}$Co-Vitamin B12 was prepared by mixing 5 ng/ml vitamin B12 (Sigma) with 0.025 microcuries/ml $^{57}$Co-cyanocobalamin (Amersham, sp. act. $10^5$ cpm/ng). 750 microliters of saline were mixed with 350 microliters of $^{57}$Co-vitamin B12 and with 100 microliters final volume of the sample. 0.5 ml of albumin-coated charcoal was then added and the test tubes were centrifuged for 2 minutes at 10,000×g at room temperature. 1 ml of the supernatant was collected and counted in a Packard autogamma scintillation counter™ (Packard Instrument Co., Downers Grove, Ill.) to determine the amount of bound $^{57}$Co-B12 in each sample.

Protein was determined as described in (20) using bovine serum albumin as standard. To prevent Triton X-100™ interference with the assay, 0.1% sodium dodecyl sulfate was added to the alkaline copper solution (21). Percoll™ at the concentration present in the fractions did not affect the assay.

To assay myeloperoxidase, 200 microliters of each fraction were diluted 5-fold in relaxation buffer containing 0.2% Triton X-100, and introduced into the sample compartment of a Perkin-Elmer 557 double beam spectrophotometer (Coleman Instruments Division, Oak Brook, Ill.). Absorption spectra, from 400 to 600 nm, of oxidized fractions versus fractions reduced with dithionite were then measured ($E_{472}$ nm=75 mM$^{-1}$ cm$^{-1}$) (14).

Preparation of an azurophil-derived bactericidal factor (ADBF)

Fractions from the Percoll™ gradients corresponding to azurophil granules were pooled and Percoll was removed by centrifugation as described (16). The azurophil granule preparation was resuspended in relaxation buffer and stored either on ice at 4° C. or at −70° C. The azurophil granules stored on ice at 4° C. appeared to be intact in that no β-glucuronidase or myeloperoxidase release from the granules could be detected over 2 weeks. Freezing of the azurophil granules at −70° C. resulted in some leakiness (<20%) of the β-glucuronidase but not of the myeloperoxidase. The isolated azurophil granules were extracted with 0.05M glycine-HCl buffer pH 2.0 for 40 minutes at 25° C. The acid-extract was centrifuged at 10,000×g for 20 minutes and the supernatant used as a source of ADBF. The supernatant was either diluted in or dialyzed against the incubation medium prior to bactericidal assays. For the dialysis of ADBF-extracts, a membrane tubing of 1,000 MR cut-off (Spectra/Por, Spectrum Medical, Los Angeles, Calif.) was used. Fractions from the Percoll™ density gradients were extracted following the same procedures; Percoll had no effect on the extraction or activity of the bactericidal factor.

Bactericidal Assays

Bactericidal activity was tested against *E. coli* K12 (MC 4100) in routine assays and, where indicated, against *Salmonella typhimurium* LT2, *Pseudomonas aeruginosa* PAC and PAO, *Listeria monocytogenes, Staphylococcus aureus,* and *Streptococcus pneumoniae* type III, type II and an unencapsulated variant of the *S. pneumoniae* type II strain. Trypticase soy broth and trypticase soy agar plates were used to cultivate most bacteria. In the case of *S. pneumoniae*, Cy medium and 5% defibrinated sheep blood agar plates were used (22).

Organisms from a single colony on agar plates were inoculated into liquid medium and cultured overnight at 37° C. Aliquots of the overnight culture were inoculated into fresh nutrient broth and grown to mid-exponential phase. Bacterial cultures were then diluted into the test medium to the appropriate concentration. Most experiments were performed in 0.05M citrate buffer, pH 5.5. Control experiments showed that this buffer did not affect the viability of any of the bacteria tested except *P. aeruginosa* and *S. pneumoniae* type II, for which 0.05M phosphate buffer, pH 6.0 was used. Other buffers such as acetate, phosphate or citrate-phosphate at a concentration of 0.01M or 0.05M were used in some bactericidal assays, as specified below.

Bacteria (4×10$^4$ colony-forming units in a final volume of 200 microliters) were incubated for 30 minutes at 37° C. with various amounts of azurophil granule extract (ADBF) diluted in the incubation medium. Samples were then diluted 1:100 in M63 minimal medium (23), and spread onto agar plates. Colony forming units (CFU) were counted after incubation at 37° C. for 16 hours. Bactericidal activity was expressed as the percentage of bacteria killed after exposure to ADBF compared to control. Alternatively, 1 unit of killing activity (K.U.) is defined as the reciprocal of the dilution of ADBF preparation to kill 10$^5$ bacteria/ml in 30 minutes at 37° C. (LD$_{50}$).

Fungicidal Assays

Fungicidal activity was tested against *Candida albicans* (clinical isolate from Columbia Presbyterian Hosptial) in routine assays. Sabauraud broth™ and Sabauraud™ agar plates (Difco) were used to cultivate fungi.

Organisms from a single colony on agar plates were inoculated into liquid medium and cultured overnight at 37° C. Aliquots of the overnight culture were inoculated into fresh nutrient broth and grown to mid-exponential phase. Fungi cultures were then diluted into the test medium to the appropriate concentration. Experiments were performed in 10 mM phosphate buffer, pH 5.5.

*C. albicans* (10$^5$ colony-forming units/ml) were incubated for 60 minutes at 37° C. with various amounts of azurophil granule extract (ADBF) diluted in the incubation medium. Samples were then diluted 1:100 in M63 minimal medium (23), and spread onto agar plates. Colony forming units (CFU) were counted after incubation at 37° C. for 30 hours.

Fungitidal activity was expressed as the percentage of fungi killed after exposure to ADBF compared to control. Alternatively, 1 unit of killing activity (K.U.) is defined as the reciprocal of the dilution of ADBF preparation necessary to kill 10$^5$ fungi in 60 minutes at 37° C. (LD$_{50}$).

Isolation of azurophil granule membranes

Isolated azurophil granules in relaxation buffer (pH 7.3) from neutrophil cells were disrupted by seven cycles of freezing in an acetone-dry ice bath and thawing at 37° C., followed each time by immersion for 10 seconds in a sonicating water bath (Bransen B3,™ Heat Systems-Ultrasonic Inc. Plainview, N.Y.). A pelleted material was then obtained by centrifugation of the lysed granules at 10,000×g for 60 minutes or at 135,000×g for 6 minutes at 4° C. This pelleted material was referred to as azurophil granule membranes. Isolated granule membranes and soluble granule contents were assayed for ADBF activity after incubation with 0.05M glycine pH 2.0 as previously described.

Characterization of ADBF By Size Exclusion Chromatography

Approximately 1 mg of ADBF membrane extract was applied to a BiO-Sil TSK-125 size exclusion column equilibrated in either 50 mM glycine/0.1M NaCl, pH 2.0 or 50 mM glycine/0.5M NaCl pH 2. ADBF bactericidal and fungicidal profiles and an O.D. 280 profile were generated from the eluted fractions. Sodium dodecyl sulfatepolyacrylamide gel electrophoresis (SDS-PAGE 15%) was performed on the ADBF membrane extract and on selected fractions obtained from the size exclusion column.

Characterization of ADBF by Reverse Phase High Performance Liquid Chromatography Trifluoroacetic acid (TFA) was added to ADBF or TSK purified ADBF to 0.1% and the samples were applied to a Vydac wide pore $C_4$ (250×4 mm) reverse phase column and run on a 92 minute gradient, followed by 3 minutes at 100% and then a 2 minute wash. Solvent A was 0.1% aqueous TFA, solvent B was 0.1% TFA in HPLC grade acetonitrile. The gradient was as follows:

| TIME* | SOLVENT B |
|---|---|
| 0–2 minutes | 0% |
| 2–62 minutes | 0–48% |
| 62–92 minutes | 48–100% |
| 92–95 minutes | 100% |
| 95–97 minutes | 0% |

The equipment utilized was a Beckman reverse phase HPLC system™ consisting of a Vydac™ wide pore $C_4$ (250×4 mm) reverse phase column, two 110B pumps, a 421A controller, a 210A injector, a 2 ml sample loop, a 163 variable wavelength detector, a 2112 Redirac fraction collector,™ and a Kipp and Zonen BD 41 chart recorder™. The detector setting was 214 nm, 0–0.5 absorbance units full scale (AUFS) and the peak fractions were collected manually.

Sequence Analysis of Polypeptides Derived From ADBF

RPHPLC purified ADBF and TSK/RPHPLC purified ADBF were concentrated to 50 microliters on a Speed Vac® and loaded onto an Applied Biosystems 477A™ pulse liquid phase sequenator, Phenylthiohydantoin (PTH) analysis was performed on line using an Applied Biosystems Model 120A PTH Analyzer™.

Amino Acid Analysis of Polypeptides Derived From ADBF

PTC amino acid analysis of polypeptides was obtained by 1 hour hydrolysis with 6.0N HCl at 150° C. using a Waters Picotag® system equipped with a Beckman™ HPLC system.

Culturing HL60 cells

HL60 cells (24,25) were grown in suspension cultures containing basal media (serum free) supplemented with insulin and transferrin. Cells were grown to a density of $2 \times 10^6$ cells/ml and harvested by centrifugation. The cell pellet was resuspended to $1 \times 10^8$ cells/ml for further fractionation.

Preparation and screening of HL60 cDNA libraries

Human HL60 cells (ATCC CCL 240) were grown as specified to $1 \times 10^6$ cells/ml in DMEM containing 5% fetal calf serum. For the induced library, cells were treated with 1% DMSO 40 hours prior to harvest. The cells were harvested at 4° C. and washed twice with phosphate-buffered saline (PBS). The cell pellets were recovered, homogenized in buffer containing 20 mM vanadyl complex (Bethesda Research Laboratories) and 0.2% Nonidet P-40™, and centrifuged for 10 minutes at 14,000 rpm in a Beckman JS-13™ rotor. RNA was prepared from the supernatant using phenol-chloroform extraction and the total RNA obtained was subjected to oligo-dT affinity chromatography to obtain mRNA.

The total mRNA preparations from the induced and uninduced cells were used as a template to prepare cDNA libraries in λgt10, as described in (26), but with second strand synthesis performed according to the method described in (27). The resulting cDNA was ligated with a synthetic oligonucleotide (CCGGAATTCCGG, Bethesda Research Laboratories) and then digested with EcoR1. The cDNA was size fractionated and purified using polyacrylamide gels and inserted into the EcoR1 site of λgt10. Several million phage were obtained from both induced and uninduced RNA. Triplicate filter lifts were prepared and phage were screened under conditions of moderate stringency (6×SSC, 35° C.) with a 5'-end labeled mixture of a 14 mer pool of 16 oligonucleotides prepared using the reverse complement of the sequence encoding amino acids 31–35 of peak 5b. (see FIG. 11).

| | | | | | | | | |
|---|---|---|---|---|---|---|---|---|
| Ile—His—Asn—Phe—Asn—Ile—Asn—Tyr | | | | | | | | (SEQ ID NO: 4) |
| CAT ATT TTT AAT AT | | | | | | | | (SEQ ID NO: 5) |
| C   C   C   C | | | | | | | | |
| PROBE   3'GTA TTA AAA TTA TA | | | | | | | | (SEQ ID NO: 6) |
| G   G   G   G | | | | | | | | |

Results

Subcellular distribution of bactericidal factor

Figure 1A:
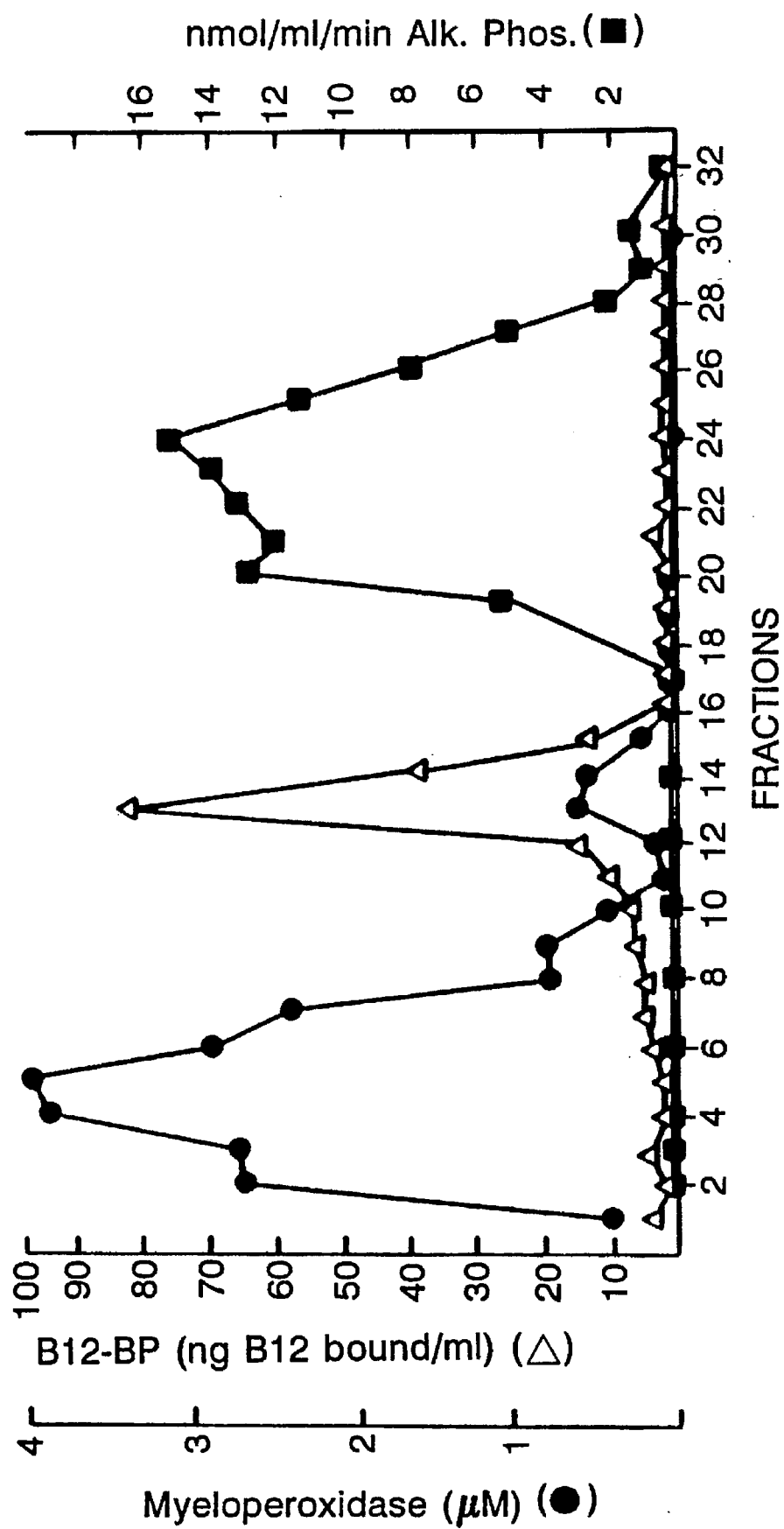
FIGS. 1A and 1B. Subcellular distribution of bactericidal activity in human neutrophils FIG. 1A Distribution of markers for azurophil granules (myeloperoxidase), specific granules (vitamin B12-binding protein), and plasma membrane (alkaline phosphate).

To determine the subcellular location of ADBF in neutrophils, the neutrophils were fractionated using the method described (16). Neutrophils were treated with 5 mM diisopropylfluorophosphate (DFP) prior to fractionation because DFP, a potent serine protease inhibitor, has been shown to inhibit proteolysis very effectively in PMN extracts (28,29). $10^9$ DFP-treated cells were disrupted by nitrogen cavitation, and the postnuclear supernatant was centrifuged on a discontinuous Percoll density gradient. Each fraction of the gradient was assayed for specific markers of azurophil granules (myeloperoxidase), specific granules (vitamin B12-binding protein) and plasma membrane (alkaline phosphatase). As shown in FIG. 1A, the method resulted in efficient separation of these three compartments. Azurophil granules showed no contamination by markers of specific granules or plasma membranes. Specific granules were not contaminated by plasma membranes but had some contamination by azurophil granules, as indicated by the presence of 10% of the myeloperoxidase in this peak.

Bactericidal activity, obtained by extraction of cellular fractions at pH 2.0, distributed as shown in Table I.

TABLE I

Distribution of BF in Human Neutrophils

| Purification step | Volume (ml) | Protein (mg/ml) | K.U.[a] | S.A.[b] | Yield (%) |
|---|---|---|---|---|---|
| Cavitate | 9.8 | 0.6 | 1500 | 2500 | 100 |
| Pellet | 2.0 | 0.6 | 450 | 750 | 6 |
| S1[c] | 8.8 | 0.46 | 1280 | 2780 | 97 |
| S2[d] | 8.0 | 0.26 | 6.5 | 25 | 0.8 |
| γ (plasma membrane) | 3.0 | 0.13 | 4.0 | 30 | 0.4 |
| β (specific granules) | 3.0 | 0.21 | 2.5 | 12.5 | 4.5 |
| α (azurophil granules) | 3.0 | 0.20 | 1430 | 7140 | 86 |

Figure 1B:
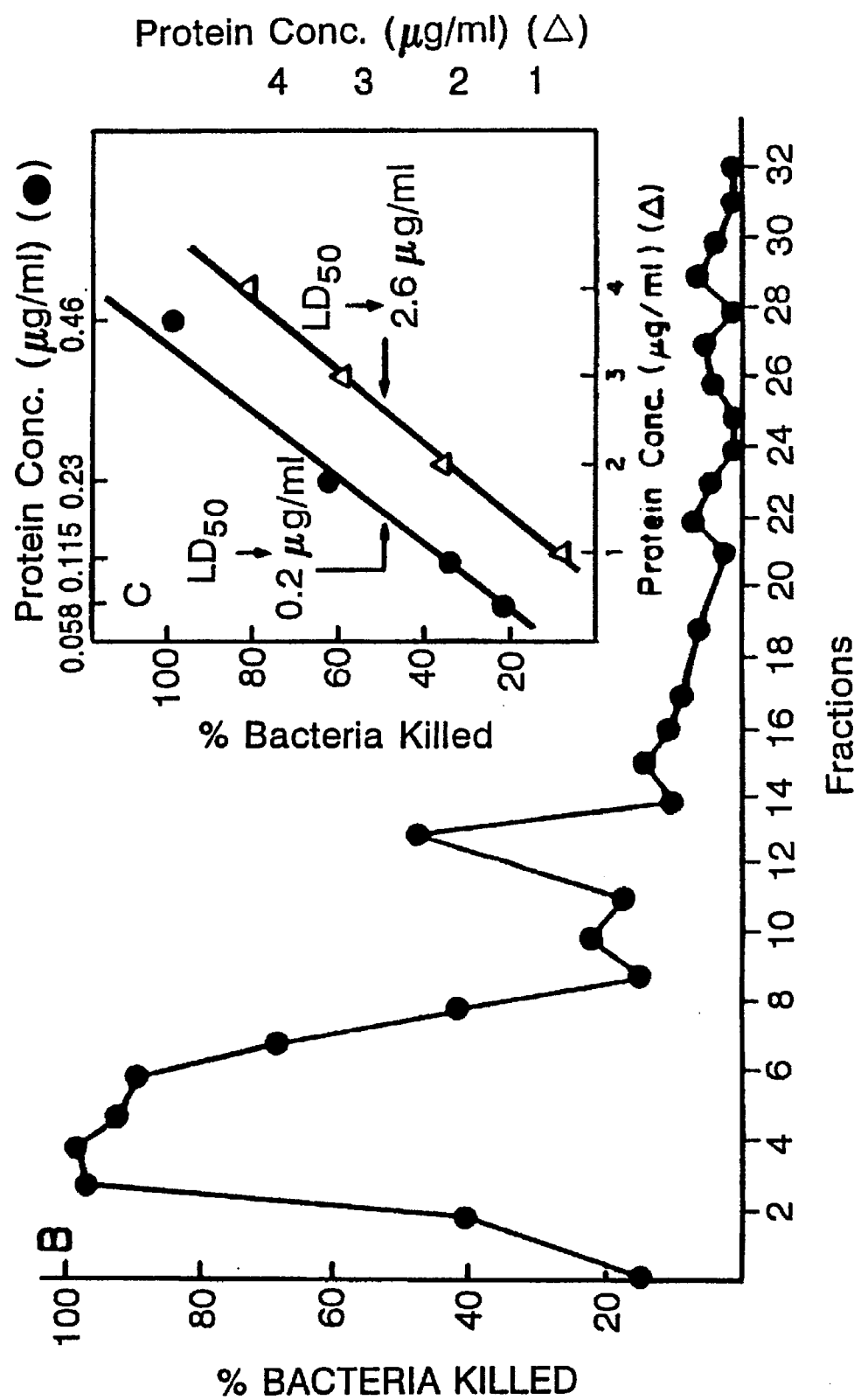

[a]Killing units
[b]Specific activity (KU/mg protein)
[c]Postnuclear supernatant
[d]Cytosol The majority of activity of the cavitate was present in the postnuclear supernatant ($S_1$). 6% of activity was associated with the nuclear fraction, perhaps due to adherence of a few granules to nuclei. The location of the bactericidal factor in the granule fraction was further indicated by a specific activity which was twice that of the unfractionated cavitate. As shown in FIG. 1, more than 90% of the bactericidal factor was present in the azurophil granule fraction. The low level of activity present in the specific granule fraction could be attributed to the 10% contamination by azurophil granules, as detected by the myeloperoxidase assay (see FIG. 1A). Indeed, approximately 10 times more protein from the specific fraction than from the azurophil granule fraction was required to kill 50% of the bacteria (inset, FIG. 1B).

Membrane association of bactericidal factors

Figure 2:
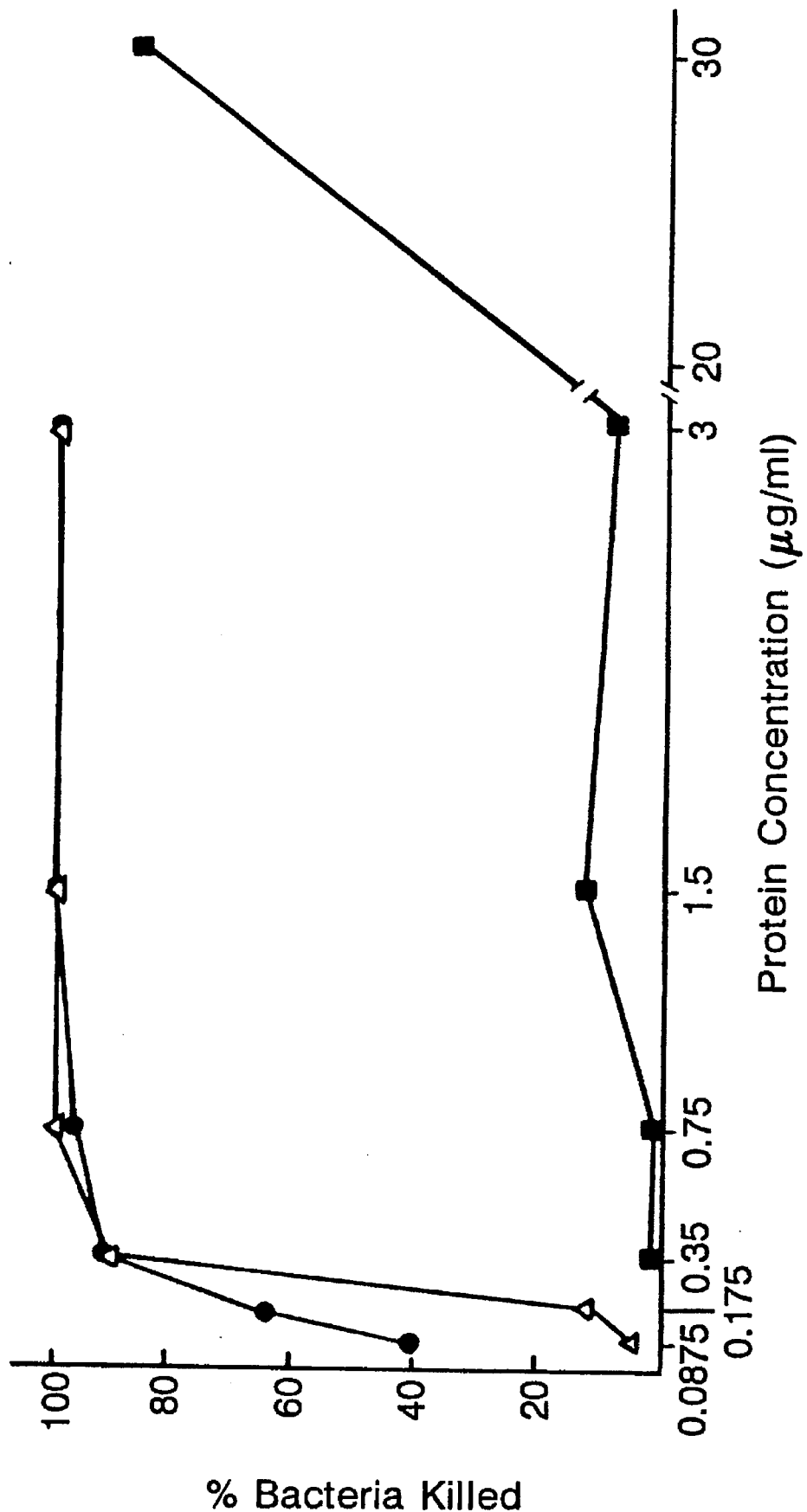
FIG. 2. Membrane association of an azurophil derived bactericidal factor (ADBF)

To determine the location of ADBF within neutrophil azurophil granules, intact purified granules were lysed at neutral pH by repeated freeze-thaw and sonication. The disrupted granules were centrifuged and soluble granule contents were separated from pelleted granule membranes. Under these conditions, more than 90% of β-glucuronidase and myeloperoxidase were found in the supernatant fraction (data not shown). In contrast, 98% of ADBF was associated with azurophil membranes, as shown in FIG. 2.

The ability of a number of agents to release ADBF from azurophil membranes was also examined. ADBF activity was assayed in the supernatant, and the pellet obtained after centrifugation of azurophil membranes was treated with buffers of varying pH. FIG. 3 shows that less than 10% of ADBF activity was released from the membrane at pH 5.0–7.0, 50% at pH 4.0 and 100% at pH 2.0–3.0. The extraction of the bactericidal factor from intact azurophil granules followed the same pH curve (data not shown). Other agents commonly used to solubilize peripheral and integral membrane proteins were then tested (see Table II below). 50 microliters of azurophil membranes (0.5 micrograms protein/microliters) were incubated at 25° C. for 40 minutes in 200 microliters of the various agents above. After centrifugation at 10,000×g for 20 minutes (4° C.), the supernatants were collected, dialysed against 0.05M citrate pH 5.5 and tested for protein and bactericidal activity. Pellets were washed 3 times with ice-cold 0.05M phosphate pH 7.0, incubated at 25° C. for 40 minutes with 0.05M glycine pH 2.0, centrifuged and the supernatants assayed for protein and killing activity. For Triton X-114™ treatment of azurophil membranes, the procedure described in (30) was followed.

sodium bicarbonate pH 11 released the bactericidal factor from the granule membrane.

Triton X-114 has been used on isolated membranes or whole cells to separate integral membrane proteins from hydrophilic proteins; hydrophilic proteins are recovered in the aqueous phase, whereas amphophilic integral membrane proteins are found in the detergent phase after the phase separation of this detergent at 20° C. and greater (30,31). When azurophil membranes were extracted with Triton X-114™, 87% of ADBF activity partitioned with the detergent phase.

ADBF-activity in vitro depends on release from the azurophil membrane

Azurophil membranes were treated at pH 2.0, which solubilizes ADBF, or at pH 5.5, which represents intralysosomal pH (32–34) but does not release ADBF from the membrane (see FIG. 3). Bactericidal activity was then assayed at pH 5.5 in total membranes, and in the supernatant and pellet fractions obtained after centrifugation of the membranes treated at both pH's. ADBF from membranes treated at pH 5.5 (membrane-bound ADBF: 1 K.U.) was 10 times less active than ADBF from membranes treated. at pH 2.0 (soluble ADBF: 11.6 K.U.). Bactericidal activity could be recovered almost completely from membranes treated at pH 5.5 by reextraction at pH 2.0 (see Table II above).

Effect of dose, time, bacterial growth status, and buffer

ADBF activity was linear with respect to protein concentration over the range of 0.3 to 30 micrograms/ml (FIG. 1B and further data not shown). The effect of bacterial concentration is shown in FIG. 4: up to $10^7$ bacteria/ml could be killed by 30 micrograms/ml of ADBF-containing extract in 30 minutes at 37° C. Killing was rapid: 50% of the cells were killed within 5 minutes at 37° C. by the azurophil granule extract containing 1.4 micrograms protein/ml (FIG. 5). The physiological state of the bacteria incubated in the test medium did not affect their susceptibility to ADBF. Thus, bacteria in exponential growth or in stationary phase were

TABLE II

Effect of pH, Ionic Strength and Surface-Active Agents on the Release of ADBF from the Azurophil Membrane

| Azurophil membranes treated with: | | Bactericidal acitivity of material released into supernatant (killing units) | Bactercidial activi of material remaini in membrane pellet (killing units) |
| --- | --- | --- | --- |
| Buffer | Additional Agents | | |
| 0.05M glycine pH 2.0 | — | 1430 | <10 |
| 0.05M citrate pH 5.5 | — | 20 | 1190 |
| 0.1M sodium bicarbonate, pH 11.0 | — | <10 | 1100 |
| 0.05M phosphate pH 7.0 | 2M NaCl | <10 | 820 |
| None | 6M urea | <10 | 1310 |
| 0.05M phosphate pH 7.0 | 1% Triton X-100 | 1310 | <110 |
| 0.01M Tris pH 7.4 | 0.15M NaCl 0.05% Triton X-114 | 170[a] 1200[b] | N/A[c] |

[a]aqueous phase
[b]detergent phase
[c]not applicable

As shown in Table II, treatment of the azurophil membranes with 1% Triton X-100 released ADBF activity as effectively as acid. In contrast, neither 6M urea nor 0.1M equally sensitive. The addition of glucose (20 mM) to the incubation medium did not affect ADBF activity. The killing activity of ADBF was approximately the same when citrate, acetate or phosphate salts were used as a buffer (data not shown).

Effect of pH and divalent cations

Since it has been shown that phagosomes rapidly reach and maintain a pH value of 5.5 during intracellular killing of bacteria in vivo (21–23), the effect of pH on the bactericidal activity of ADBF in vitro was examined. ADBF was effective over a broad range of pH (5.0 to 8.0) (FIG. 6). Media more acidic than pH 5.0, which are bactericidal per se, could not be used to test ADBF killing.

Because ions such as $Mg^{2+}$ and $Ca^{2+}$ play a critical role in phagocytic processes (35) and also affect the surface properties of Gram-negative bacteria (36), the effect of these ions on ADBF bactericidal activity was also examined. $Mg^{2+}$ ions antagonized but did not completely block ADBF activity. The effect of $Mg^{2+}$ ions was maximal at 1 mM, with a 25% reduction in bactericidal activity (data not shown). In contrast, $Ca^{2+}$ ions inhibited all ADBF activity at a concentration of 25 mM and 20 mM (FIG. 7 respectively). The decrease of bactericidal activity was roughly linear with respect to calcium concentration over the range of 1 to 25 mM. Since the medium used for these tests contains citrate, which chelates divalent cations, the concentration of free cations in solution is lower than the nominal concentration. However, citrate does not bind significant amounts of magnesium and calcium at low pH (26). The addition of EDTA (1–25 mM) to the incubation medium (to chelate cations) did not affect ADBF activity (data not shown). Sodium chloride inhibited at a concentration of 0.3M or greater (FIG. 8). Physiological concentrations of sodium chloride or potassium chloride did not inhibit ADBF activity when the latter was tested at a concentration of 2.8 micrograms/ml or greater.

Bacterial Spectrum of ADBF Killing

ADBF kills both Gram positive and Gram negative bacteria (see Table III below).

TABLE III

Antibacterial Spectrum of ADBF

| Organism | Strain or Type | ADBF Activity[a] |
|---|---|---|
| Staphylococcus aureus | S27 | + |
| Staphylococcus aureus | 450 | + |
| Staphylococcus aureus | TSS-1[b] | + |
| Staphylococcus aureus | TSS-2[b] | + |
| Streptococcus pneumoniae | Type III | − |
| Streptococcus pneumoniae | Type II | + |
| Streptococcus pneumoniae | R6 | + |
| Listeria monocytogenes | 450 | (+) |
| Pseudomonas aeruginosa | PAC | + |
| Pseudomonas aeruginosa | PAO 103-0 | + |
| Salmonella typhimurium | LT2 | + |
| Escherichia coli K12 | MC 4100 | + |

[a]ADBF activity is scored according to the microgram/ml of protein in azurophil extract necessary to kill $10^5$ bacteria in 30 minutes at 37° C: +, 0.1 to 0.3 micrograms/ml; (+), 1 to 2.5 micrograms/ml; −, >20 micrograms/ml.
[b]Clinical isolates from two patients with toxic shock syndrome.

The Gram positive bacteria susceptible to ADBF killing included different strains of Staphylococcus aureus (two isolates from patients with toxic shock syndrome), β-hemolytic streptococci (with the exception of the capsulated streptococcus type III) and to some extent Listeria monocytogenes. All the Gram negative bacteria tested were killed as efficiently as E. coli.

Fungicidal Activity of ADBF

FIG. 9 shows that ADBF has fungicidal activity within the range from about 3.0 micrograms/ml to about 16.0 micrograms/ml.

Purification of ADBF

Reverse phase high performance liquid chromatography (RPHPLC) of the ADBF extract resulted in a reproducible profile containing at least 9 characteristic peaks, some of which appear as doublets (see FIG. 10A). When a portion of each fraction was dried to remove the reverse phase Solvents and then subsequently resuspended and assayed, two peaks of activity were identified as shown by the cross-hatched areas of FIG. 10A. The first activity peak overlaps two major UV peaks, designated peak 5 and peak 6, the second activity peak is associated with a single UV peak, designated peak 9. The amino acid sequence of peak 5 revealed two proteins, one with sequence identity to lysozyme (5a) and another (5b) with the N-terminal sequence shown in FIG. 11. Peak 6 contained a single novel sequence with homology to the trypsin superfamily (see FIG. 11). Peak 9 contained at least 2 proteins, i.e., 9a and 9b, having the sequences shown in FIG. 11.

Because the sequences designated 5b and 9b are identical and because both peaks are associated with bactericidal activity, applicants contemplate that this sequence along with that of 9a, is responsible for such bactericidal activity.

ADBF activity was partially purified by size exclusion chromatography on a Bio-Sil TSK-125™ column as shown in FIG. 12. Fungicidal and bactericidal activity coeluted on the column with two peaks of activity, the major peak migrating within the 50–60 kD region (fractions 31 and 32) and the minor peak within the 10–20 kD region (fraction 42). The starting material for TSK size exclusion chromatography (ADBF) and various TSK size exclusion chromatography fractions were analyzed by polyacrylamide gel electrophoresis (15%) as shown in FIG. 13.

RPHPLC of the 50–60 kD size exclusion peak (fractions 31–32) resulted in 2 peaks of activity, a minor activity peak associated with the region including peaks 4,5, and 6, and a major activity peak associated with peak 9 (FIG. 10B). Amino acid sequence analysis of peak 4 shows identity to human cathepsin G (see FIG. 11). Peak 9 corresponded to a single N-terminal sequence designated 9a in FIG. 11. Amino acid composition of purified peak 9a is shown in Table IV below.

TABLE IV

Amino Acid Analysis of Purified Peak 9a

| Amino Acid | Mole (%) |
|---|---|
| Asp | 7.3 |
| Glu | 7.4 |
| Ser | 8.8 |
| Gly | 7.3 |
| His | 1.8 |
| Arg | 4.7 |
| Thr | 4.2 |
| Ala | 11.2 |
| Pro | 6.2 |
| Tyr | 2.6 |
| Val | 8.1 |
| Met | 2.5 |
| Ile | 5.1 |

TABLE IV-continued

Amino Acid Analysis of Purified Peak 9a

| Amino Acid | Mole (%) |
|---|---|
| Leu | 10.4 |
| Phe | 5.5 |
| Lys | 7.3 |

SDS-PAGE (10%) analysis of peak 9 shows the major protein band to have a molecular weight of approximately 54,000 daltons (FIG. 14).

RPHPLC of the 10-20 kD size exclusion peak (fraction 42) resulted in a single activity peak associated with peak 5 (FIG. 10C) and having a single N-terminal sequence identical to 5b (FIG. 11). SDS-PAGE analysis of peak 5 revealed a single band on SDS-PAGE with an apparent molecular weight of 13,000 daltons (see FIG. 15).

Figure 18:
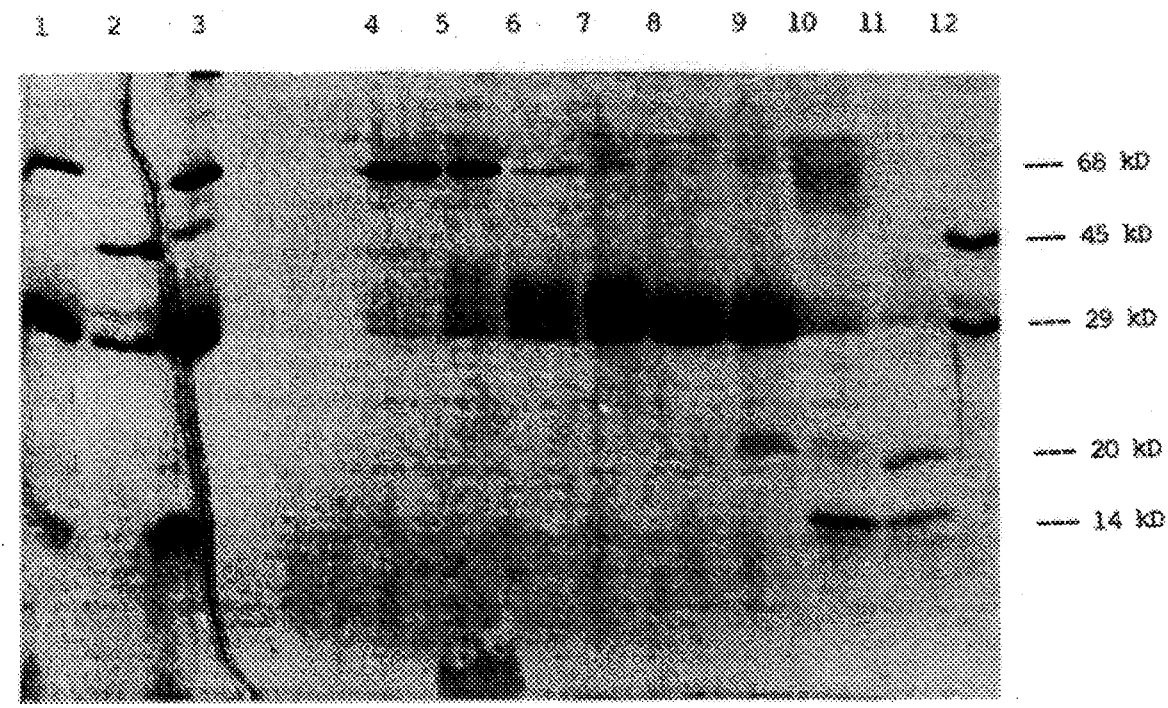

Improved resolution was obtained with TSK size exclusion chromatography using a buffer consisting of 50 mM glycine pH 2, 500 mM NaCl (see FIG. 17). Under these conditions, virtually complete separation of the 54 kD band was obtained from the 29 kD bands. Activity profiles indicated that the 54 kD protein (fractions 34-36) demonstrated only bactericidal activity and no anti-fungal activity. A region containing predominantly two proteins of 13 kD and 18 kD (fractions 42-45) contained most of the antifungal activity in addition to bactericidal activity. FIG. 18 shows the SDS-PAGE results corresponding to the various fractions.

Human HL60 cDNA libraries were screened with a probe derived from the sequence comprising amino acids 31-35 of peak 5b as described hereinabove. 16 clones were plaque-purified from the induced library. Each clone was digested with the enzyme Sau3a and the fragments inserted into the single-strand phage M13. Phage were screened by hybridization to the 14 mer pool and positive M13 phage were sequenced using the dideoxy chain termination method as described in (37). One of these clones, P-7, contained a sequence which matched exactly with that predicted by the protein sequence up to a point between amino acid residue 13 and 14 where the synthetic oligonucleotide was inserted. The EcoR1 fragment of clone P-7 was used to rescreen the uninduced library, from which 8 cDNA clones were isolated. One of these clones, designated P-FL2, was inserted into M13 vectors and sequenced. A second cDNA clone (P-FL1) was also sequenced. It was identical to P-FL2 except that its 5' end began at a point 43 base pairs after the 5' end of clone P-FL2.

Both clones (P-FL1 and P-FLZ) contain identical open reading frames encoding 220 amino acids. One N-linked glycosylation site is present (Asn-85) which could result in a larger molecule. Residues $Thr_{106}$-$Ile_{221}$ correspond exactly to the amino terminal sequence obtained for peak 5b. The predicted molecular weight for the C-terminal portion of the molecule ($Thr_{106}$-$Ile_{221}$) is about 13,000, similar to the apparent molecular weight of peak 5b on SDS-PAGE.

To more extensively characterize the antimicrobial activities of the major proteins of the azurophil granule extract, each individual reverse phase peak (shown in FIG. 10A and described in FIG. 11) was purified and tested against *E. coli*, *S. faecalis* and *C. albicans*. The concentration of each peak required to give 50% kill ($LD_{50}$) of three different test organisms is shown in Table V.

TABLE V

Summary of Activity Against Three Test Organisms

| Reverse Phase Peak I.D.** | Activity against* | | |
|---|---|---|---|
| | E. coli | S. faecalis | C. albicans |
| 1 | 225.0 | 46.0 | 2.8 |
| 2 | 3.7 | 0.6 | 0.4 |
| 3 | — | 9.0 | 0.1 |
| 4 | 0.76 | 0.3 | 0.11 |
| 5 | 0.06 | 0.03 | 0.04 |
| 6 | 0.16 | 1.9 | 1.6 |
| 7 | 0.72 | 53.0 | 5.6 |
| 8 | 0.15 | 13.0 | 5.6 |
| 9 | 0.015 | — | — |

*Expressed as $LD_{50}$ (micrograms/milliliter)
**Reverse phase fractions corresponding to peaks 1-9 were dried in the presence of 0.02% bovine serum albumin and resuspended in assay buffer

References

1. Boxer, L. A. and Morganroth, M. L. (1987) *Dis. Mon.* 33, 681.
2. Weiss, J., Elsbach, P., Olsson, I. and Odeberg, H. (1978) *J. Biol. Chem.* 253, 2664.
3. Strominger, J. L. and Ghuysen, J. M. (1967) *Science* 156, 213.
4. Odeberg, H. and Olsson, I. (1976) *Infect. Immun.* 14, 1269.
5. Blondin, J. and Janoff, A. (1976) *J. Clin. Invest.* 58, 971.
6. Ganz, T. Selsted, M. E., Szklarek, D., Harwig, S. S. L., Daher, K., Bainton, D. F. and Lehrer, R. I. (1985) *J. Clin. Invest.* 76, 1427.
7. Jong, E. C., Mahmound, A. A. F., and Klebanoff, S. J. (1981) *J. Exp. Med.* 126, 468.
8. Gleich, G. J. and Loegering, D. A. (1984) *Ann. Rev. Immunol.* 2, 429.
9. Wasmoen, T. L., Bell, M. P., Loegering, D. A., Gleich, G. J., Prendergast, P. G. and McKean, D. J. (1988) *J. Biol. Chem.* 263, 12559.
10. Barker, R. L., Gleich, L. R. and Pease, L. R. (1988) *J. Exp. Med.* 168, 1493.
11. Gleich, G. J., Loegering, D. A., Bell, M. P., Checkel, J. L., Ackerman, S. J. and McKean, D. J. (1986) *Proc. Natl. Acad. Sci.* 83, 3146.
12. Young, J. D. E., Peterson, C. G. B., Venge, P. and Cohn, Z. A. (1986) *Nature* 321, 613.
13. McLaren, D. J., McKean, J. R., Olsson, I., Venge, P. and Kay, A. B. (1981) *Parasite Immunol.* 3, 359.
14. Olsson, I., Venge, P., Spitznagel, J. K. and lehrer, R. I. (1977) *Lab Invest.* 36, 493.
15. Gleich, G. J., Loegering, D. A., Kueppers, F., Bajaj, S. P. and Mann, K. G. (1974) *J. Exp. Med.* 140, 313.
16. Borregaard, N., J. M. Heiple, E. R. Simons, and R. A. Clark. 1983. Subcellular localization of the b-cytochrome component of the human neutrophil microbicidal oxidase: translocation during activation. *J. Cell Biol* 97:52-61.
17. Boyum, A. 1968. Separation of leukocytes from blood and bone marrow. *Scand. J. Clin. Lab. Invest.* 21 (Suppl.):77-89.
18. Lindhardt, K. and K. Walter. 1963. Phosphatases (phosphomonoesterases). In Methods of Enzymic Analysis. H.-U. Bergmeyer, editor. Academic Press, Inc., New York. 779-787.
19. Gottlieb, C., K.-S. Lau, L. R. Wasserman, and V. Herbert. 1965. Rapid charcoal assay for intrinsic factor (IF), gastric juice unsaturated B12 binding capacity, antibody to IF, and serum unsaturated B12 binding capacity. *Blood* 25:875-893.

20. Lowry, O. H., N. J. Rosebrough, A. L. Farr, and R. J. Randall. 1951. Protein measurement with the Folin phenol reagent. J. Biol. Chem. 193:265–275.
21. Wang, C. S. and R. L. Smith. 1975. Lowry determination of protein in the presence of Triton X-100. Anal. Biochem. 63:414–417.
22. Tomasz, A. 1968. Biological consequences of the replacement of choline by ethanolamine in the cell wall of pneumococcus: chain formation, loss of transformability, and loss of autolysis. Proc. Natl. Acad. Sci. U.S.A. 59:86–93.
23. Miller, J. H. 1972. *Experiments in Molecular Genetics.* Cold Spring Harbor Laboratory, New York. pp. 137–140.
24. Collins, S. J., Gallo R. C., and Gallagher, R. E., 1977. Continous growth and differentiation of human myeloid leukaemic cells in suspension culture. Nature 270: 347–349.
25. Collins, S. J., Ruscetti, F. W., Gallagher, R. E., and Gallo, R. C., 1978. Terminal Differentiation of human promyelocytic leukemia cells induced by dimethyl sulfoxide and other polar compounds. P30c. Natl. Acad. Sci. U.S.A. 75: 2458–2492.
26. Huynh, T. V., et al., 1984. *DNA Cloning Techniques: A Practical Approach*, Glover,21. ed., IRL, Oxford.
27. Gubler, V., et al., 1983. Gene 25: 263–269.
28. Amrein, P. C. and T. P Stossel. 1980. Prevention of degradation of human polymorphonuclear leukocyte proteins by diisopropylfuorophosphate. Blood 56:442–447.
29. Shafter, W. M., L. E. Martin, and J. K. Sptiznagel. 1984. Cationic antimicrobial proteins isolated from human neutrophil granulocytes in the presence of diisopropylflourophosphate. Infect. Immun. 15.
30. Bordier, C. 1981. Phase separation of integral membrane proteins in Triton X-114 solution. J. Biol. Chem. 256:1604–1607.
31. Lewis, V., S. A. Green, M. Marsh, P. Vihko, A. Helenius, and I. Mellman. 1985. Glycoproteins of the lysosomal membrane. J. Cell Biol. 100:1839–1847.
32. Geisow, M. J., P. D'Arcy Hart, and M. R. Young. 1981. Temporal changes of lysosome and phagosome pH during phagolysosome formation in macrophages: Studies by fluorescence spectroscopy J. Cell. Biol. 89:645–652.
33. McNeil, P. L., L. Tanasugarn, J. B. Meigs, and D. K. Taylor. 1983. Acidification of phagosomes is initiated before lysosomal enzyme activity is detected. J. Cell Biol. 97:692–702.
34. Horwitz, M. A. and F. R. Maxfield. 1984. *Legionella pneumophila* inhibits acidification of its phagosome in human monocytes. J. Cell Biol. 99:1936–1943.
35. Silverstein, S. C., R. M. Steinman and Z. A. Cohn. 1977. Endocytosis. Ann. Rev. Biochem. 46:669–722.
36. Nikaido, H. and M. Vaara. 1985. Molecular basis of bacterial outer membrane permeability. Microbiol. Rev. 49:1–32.
37. Smith, A. J. H., 1980. Meth. Enzym. 65: 560–580. 49:29–14.

---

What is claimed is:

1. An isolated and purified cDNA fragment comprising the nucleotide sequence of SEQ ID NO:23.

2. A vector which comprises the cDNA molecule of claim 1.

3. A vector of claim 2 which comprises a plasmid.

4. A transformed host cell which comprises an in vitro cell transformed with the vector of claim 2.

5. A method for producing a protein antimicrobial agent which comprises a human polymorphonuclear leukocyte polypeptide encoded by the nucleotide sequence of SEQ ID NO:23, the method comprising growing in vitro a transformed mammalian host cell comprising a mammalian expression vector, the vector comprising the cDNA of claim 1, and recovering the resulting human polymorphonuclear leukocyte polypeptide.

6. An isolated and purified cDNA fragment comprising nucleotides 364 to 483 of SEQ ID NO:23.

7. A vector which comprises the cDNA molecule of claim 6.

8. A vector of claim 7 which comprises a plasmid.

9. A transformed host cell which comprises an in vitro cell transformed with the plasmid of claim 7.

10. A method for producing a protein antimicrobial agent which comprises the human polymorphonuclear leukocyte polypeptide encoded by nucleotides 364 to 483 of SEQ ID NO:23, the method comprising growing in vitro a transformed mammalian host cell comprising a mammalian expression vector, the vector comprising the cDNA of claim 6, and recovering the resulting human polymorphonuclear leukocyte polypeptide.

* * * * *

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
        ( A ) LENGTH: 38 amino acids
        ( B ) TYPE: amino acid
        ( C ) STRANDEDNESS: unknown
        ( D ) TOPOLOGY: unknown ( i i ) MOLECULE TYPE: protein ( v ) FRAGMENT TYPE: N-terminal ( x i ) SEQUENCE DESCRIPTION: SEQ ID NO:1:

```
Val  Asn  Pro  Gly  Val  Val  Val  Arg  Ile  Ser  Gln  Lys  Gly  Leu  Asp  Tyr
1              5                        10                       15
Ala  Ser  Gln  Gln  Gly  Thr  Ala  Ala  Leu  Gln  Xaa  Xaa  Leu  Lys  His  Ile
               20                       25                       30
Lys  Ile  Pro  Asp  Tyr  Leu
          35
```

( 2 ) INFORMATION FOR SEQ ID NO:2:

( i ) SEQUENCE CHARACTERISTICS:
        ( A ) LENGTH: 25 amino acids
        ( B ) TYPE: amino acid
        ( C ) STRANDEDNESS: unknown
        ( D ) TOPOLOGY: unknown ( i i ) MOLECULE TYPE: protein ( v ) FRAGMENT TYPE: N-terminal ( x i ) SEQUENCE DESCRIPTION: SEQ ID NO:2:

Ile Val Gly Gly Arg Lys Ala Arg Pro Arg Gln Phe Pro Phe Leu Ala
1               5                   10                  15

Ser Ile Gln Asn Gln Gly Arg His Phe
            20              25

( 2 ) INFORMATION FOR SEQ ID NO:3:

( i ) SEQUENCE CHARACTERISTICS:
        ( A ) LENGTH: 20 amino acids
        ( B ) TYPE: amino acid
        ( C ) STRANDEDNESS: unknown
        ( D ) TOPOLOGY: unknown ( i i ) MOLECULE TYPE: protein ( v ) FRAGMENT TYPE: N-terminal ( x i ) SEQUENCE DESCRIPTION: SEQ ID NO:3:

Ile Val Gly Gly His Glu Ala Xaa Xaa Pro Ser Asp Pro Tyr Met Asp
1               5                   10                  15

Ser Leu Asp Met
            20

( 2 ) INFORMATION FOR SEQ ID NO:4:

( i ) SEQUENCE CHARACTERISTICS:
        ( A ) LENGTH: 8 amino acids
        ( B ) TYPE: amino acid
        ( C ) STRANDEDNESS: unknown
        ( D ) TOPOLOGY: unknown ( i i ) MOLECULE TYPE: protein ( v ) FRAGMENT TYPE: N-terminal ( x i ) SEQUENCE DESCRIPTION: SEQ ID NO:4:

Ile His Asn Phe Asn Ile Asn Tyr
1               5

( 2 ) INFORMATION FOR SEQ ID NO:5:

( i ) SEQUENCE CHARACTERISTICS:
        ( A ) LENGTH: 14 base pairs
        ( B ) TYPE: nucleic acid
        ( C ) STRANDEDNESS: unknown
        ( D ) TOPOLOGY: unknown ( i i ) MOLECULE TYPE: mRNA ( x i ) SEQUENCE DESCRIPTION: SEQ ID NO:5:

CATAATTTTA ATAT    14

( 2 ) INFORMATION FOR SEQ ID NO:6:

( i ) SEQUENCE CHARACTERISTICS:
        ( A ) LENGTH: 14 base pairs
        ( B ) TYPE: nucleic acid
        ( C ) STRANDEDNESS: unknown
        ( D ) TOPOLOGY: unknown ( i i ) MOLECULE TYPE: cDNA ( x i ) SEQUENCE DESCRIPTION: SEQ ID NO:6:

ATATTAAAAT TATG    14

( 2 ) INFORMATION FOR SEQ ID NO:7:

(i) SEQUENCE CHARACTERISTICS:
    (A) LENGTH: 40 amino acids
    (B) TYPE: amino acid
    (C) STRANDEDNESS: unknown
    (D) TOPOLOGY: unknown (ii) MOLECULE TYPE: protein (v) FRAGMENT TYPE: N-terminal (xi) SEQUENCE DESCRIPTION: SEQ ID NO:7:

```
Thr Cys Arg Tyr Leu Leu Val Arg Ser Leu Gln Thr Phe Ser Gln Ala
1               5                   10                  15
Trp Phe Thr Cys Arg Arg Cys Tyr Arg Gly Asn Leu Val Ser Ile His
            20                  25                  30
Asn Phe Asn Ile Asn Tyr Arg Ile
            35                  40
```

(2) INFORMATION FOR SEQ ID NO:8:

(i) SEQUENCE CHARACTERISTICS:
    (A) LENGTH: 20 amino acids
    (B) TYPE: amino acid
    (C) STRANDEDNESS: unknown
    (D) TOPOLOGY: unknown (ii) MOLECULE TYPE: protein (v) FRAGMENT TYPE: N-terminal (xi) SEQUENCE DESCRIPTION: SEQ ID NO:8:

```
Ile Val Gly Gly His Glu Ala Gln Pro His Ser Arg Pro Tyr Met Ala
1               5                   10                  15
Ser Leu Glu Met
            20
```

(2) INFORMATION FOR SEQ ID NO:9:

(i) SEQUENCE CHARACTERISTICS:
    (A) LENGTH: 20 amino acids
    (B) TYPE: amino acid
    (C) STRANDEDNESS: unknown
    (D) TOPOLOGY: unknown (ii) MOLECULE TYPE: protein (v) FRAGMENT TYPE: N-terminal (xi) SEQUENCE DESCRIPTION: SEQ ID NO:9:

```
Ile Val Gly Gly Arg Lys Ala Arg Pro His Gln Phe Pro Phe Leu Ala
1               5                   10                  15
Ser Ile Gln Asn
            20
```

(2) INFORMATION FOR SEQ ID NO:10:

(i) SEQUENCE CHARACTERISTICS:
    (A) LENGTH: 20 amino acids
    (B) TYPE: amino acid
    (C) STRANDEDNESS: unknown
    (D) TOPOLOGY: unknown (ii) MOLECULE TYPE: protein (v) FRAGMENT TYPE: N-terminal (xi) SEQUENCE DESCRIPTION: SEQ ID NO:10:

```
Ile Val Gly Gly His Glu Ala Gln Pro His Ser Arg Pro Tyr Met Ala
1               5                   10                  15
```

```
    Ser   Leu   Glx   Met
                      20
```

( 2 ) INFORMATION FOR SEQ ID NO:11:

( i ) SEQUENCE CHARACTERISTICS:
        ( A ) LENGTH: 15 amino acids
        ( B ) TYPE: amino acid
        ( C ) STRANDEDNESS: unknown
        ( D ) TOPOLOGY: unknown ( i i ) MOLECULE TYPE: protein ( v ) FRAGMENT TYPE: N-terminal ( x i ) SEQUENCE DESCRIPTION: SEQ ID NO:11:

```
    Cys   Tyr   Cys   Arg   Ile   Pro   Ala   Cys   Ile   Ala   Gly   Glu   Arg   Arg   Tyr
    1                       5                       10                                  15
```

( 2 ) INFORMATION FOR SEQ ID NO:12:

( i ) SEQUENCE CHARACTERISTICS:
        ( A ) LENGTH: 15 amino acids
        ( B ) TYPE: amino acid
        ( C ) STRANDEDNESS: unknown
        ( D ) TOPOLOGY: unknown ( i i ) MOLECULE TYPE: protein ( v ) FRAGMENT TYPE: N-terminal ( x i ) SEQUENCE DESCRIPTION: SEQ ID NO:12:

```
    Val   Xaa   Ser   Xaa   Arg   Leu   Val   Phe   Xaa   Arg   Arg   Thr   Gly   Leu   Arg
    1                       5                       10                                  15
```

( 2 ) INFORMATION FOR SEQ ID NO:13:

( i ) SEQUENCE CHARACTERISTICS:
        ( A ) LENGTH: 15 amino acids
        ( B ) TYPE: amino acid
        ( C ) STRANDEDNESS: unknown
        ( D ) TOPOLOGY: unknown ( i i ) MOLECULE TYPE: protein ( v ) FRAGMENT TYPE: N-terminal ( x i ) SEQUENCE DESCRIPTION: SEQ ID NO:13:

```
    Xaa   Pro   Pro   Gln   Phe   Thr   Arg   Ala   Gln   Trp   Phe   Ala   Ile   Gln   His
    1                       5                       10                                  15
```

( 2 ) INFORMATION FOR SEQ ID NO:14:

( i ) SEQUENCE CHARACTERISTICS:
        ( A ) LENGTH: 15 amino acids
        ( B ) TYPE: amino acid
        ( C ) STRANDEDNESS: unknown
        ( D ) TOPOLOGY: unknown ( i i ) MOLECULE TYPE: protein ( v ) FRAGMENT TYPE: N-terminal ( x i ) SEQUENCE DESCRIPTION: SEQ ID NO:14:

```
    Ile   Ile   Gly   Gly   Arg   Glu   Ser   Arg   Pro   His   Ser   Arg   Pro   Tyr   Met
    1                       5                       10                                  15
```

( 2 ) INFORMATION FOR SEQ ID NO:15:

( i ) SEQUENCE CHARACTERISTICS:

(A) LENGTH: 15 amino acids
(B) TYPE: amino acid
(C) STRANDEDNESS: unknown
(D) TOPOLOGY: unknown (ii) MOLECULE TYPE: protein (v) FRAGMENT TYPE: N-terminal (xi) SEQUENCE DESCRIPTION: SEQ ID NO:15:

```
Lys Val Phe Glu Arg Xaa Glu Leu Ala Arg Thr Leu Lys Arg Leu
1               5                   10                  15
```

(2) INFORMATION FOR SEQ ID NO:16:

(i) SEQUENCE CHARACTERISTICS:
(A) LENGTH: 15 amino acids
(B) TYPE: amino acid
(C) STRANDEDNESS: unknown
(D) TOPOLOGY: unknown (ii) MOLECULE TYPE: protein (v) FRAGMENT TYPE: N-terminal (xi) SEQUENCE DESCRIPTION: SEQ ID NO:16:

```
Thr Cys Arg Tyr Leu Leu Val Arg Ser Leu Gln Thr Phe Ser Gln
1               5                   10                  15
```

(2) INFORMATION FOR SEQ ID NO:17:

(i) SEQUENCE CHARACTERISTICS:
(A) LENGTH: 15 amino acids
(B) TYPE: amino acid
(C) STRANDEDNESS: unknown
(D) TOPOLOGY: unknown (ii) MOLECULE TYPE: protein (v) FRAGMENT TYPE: N-terminal (xi) SEQUENCE DESCRIPTION: SEQ ID NO:17:

```
Ile Val Gly Gly Arg Lys Ala Arg Pro Arg Gln Phe Pro Phe Leu
1               5                   10                  15
```

(2) INFORMATION FOR SEQ ID NO:18:

(i) SEQUENCE CHARACTERISTICS:
(A) LENGTH: 15 amino acids
(B) TYPE: amino acid
(C) STRANDEDNESS: unknown
(D) TOPOLOGY: unknown (ii) MOLECULE TYPE: protein (v) FRAGMENT TYPE: N-terminal (xi) SEQUENCE DESCRIPTION: SEQ ID NO:18:

```
Ile Val Gly Gly His Glu Ala Xaa Xaa Pro Ser Asp Pro Tyr Met
1               5                   10                  15
```

(2) INFORMATION FOR SEQ ID NO:19:

(i) SEQUENCE CHARACTERISTICS:
(A) LENGTH: 15 amino acids
(B) TYPE: amino acid
(C) STRANDEDNESS: unknown
(D) TOPOLOGY: unknown (ii) MOLECULE TYPE: protein (v) FRAGMENT TYPE: N-terminal ( x i ) SEQUENCE DESCRIPTION: SEQ ID NO:19:

Val Asn Cys Glu Thr Ser Cys Val Gln Gln Pro Pro Cys Phe Pro
1               5                   10                  15

( 2 ) INFORMATION FOR SEQ ID NO:20:

( i ) SEQUENCE CHARACTERISTICS:
      ( A ) LENGTH: 15 amino acids
      ( B ) TYPE: amino acid
      ( C ) STRANDEDNESS: unknown
      ( D ) TOPOLOGY: unknown ( i i ) MOLECULE TYPE: protein ( v ) FRAGMENT TYPE: N-terminal ( x i ) SEQUENCE DESCRIPTION: SEQ ID NO:20:

Ile Val Gly Gly Arg Arg Ala Arg Pro His Ala Xaa Pro Xaa Met
1               5                   10                  15

( 2 ) INFORMATION FOR SEQ ID NO:21:

( i ) SEQUENCE CHARACTERISTICS:
      ( A ) LENGTH: 15 amino acids
      ( B ) TYPE: amino acid
      ( C ) STRANDEDNESS: unknown
      ( D ) TOPOLOGY: unknown ( i i ) MOLECULE TYPE: protein ( v ) FRAGMENT TYPE: N-terminal ( x i ) SEQUENCE DESCRIPTION: SEQ ID NO:21:

Val Asn Pro Gly Val Val Arg Ile Ser Gln Lys Gly Leu Asp
1               5                   10                  15

( 2 ) INFORMATION FOR SEQ ID NO:22:

( i ) SEQUENCE CHARACTERISTICS:
      ( A ) LENGTH: 15 amino acids
      ( B ) TYPE: amino acid
      ( C ) STRANDEDNESS: unknown
      ( D ) TOPOLOGY: unknown ( i i ) MOLECULE TYPE: protein ( v ) FRAGMENT TYPE: N-terminal ( x i ) SEQUENCE DESCRIPTION: SEQ ID NO:22:

Thr Cys Arg Tyr Leu Leu Val Arg Ser Leu Gln Thr Phe Ser Gln
1               5                   10                  15

( 2 ) INFORMATION FOR SEQ ID NO:23:

( i ) SEQUENCE CHARACTERISTICS:
      ( A ) LENGTH: 842 base pairs
      ( B ) TYPE: nucleic acid
      ( C ) STRANDEDNESS: unknown
      ( D ) TOPOLOGY: unknown ( i i ) MOLECULE TYPE: cDNA ( i x ) FEATURE:
      ( A ) NAME/KEY: CDS
      ( B ) LOCATION: 49..711
      ( D ) OTHER INFORMATION:

( x i ) SEQUENCE DESCRIPTION: SEQ ID NO:23:

GGGAAGATCT AAACACCCAG GAAGGTCTCT GGGTGGGATA AAGCCAAG ATG AAA CTC    57

```
                                                        Met Lys Leu
                                                         1
CCC TTA CTT CTG GCT CTT CTA TTT GGG GCA GTT TCT GCT CTT CAT CTA      105
Pro Leu Leu Leu Ala Leu Leu Phe Gly Ala Val Ser Ala Leu His Leu
     5               10                  15

AGG TCT GAG ACT TCC ACC TTT GAG ACC CCT TTG GGT GCT AAG ACG CTG      153
Arg Ser Glu Thr Ser Thr Phe Glu Thr Pro Leu Gly Ala Lys Thr Leu
 20              25                  30                      35

CCT GAG GAT GAG GAG ACA CCA GAG CAG GAG ATG GAG GAG ACC CCT TGC      201
Pro Glu Asp Glu Glu Thr Pro Glu Gln Glu Met Glu Glu Thr Pro Cys
                 40                  45                  50

AGG GAG CTG GAG GAA GAG GAG GAG TGG GGC TCT GGA AGT GAA GAT GCC      249
Arg Glu Leu Glu Glu Glu Glu Glu Trp Gly Ser Gly Ser Glu Asp Ala
             55                  60                  65

TCC AAG AAA GAT GGG GCT GTT GAG TCT ATC TCA GTG CCA GAT ATG GTG      297
Ser Lys Lys Asp Gly Ala Val Glu Ser Ile Ser Val Pro Asp Met Val
         70                  75                  80

GAC AAA AAC CTT ACG TGT CCT GAG GAA GAG GAC ACA GTA AAA GTG GTG      345
Asp Lys Asn Leu Thr Cys Pro Glu Glu Glu Asp Thr Val Lys Val Val
     85                  90                  95

GGC ATC CCT GGG TGC CAG ACC TGC CGC TAC CTC CTG GTG AGA AGT CTT      393
Gly Ile Pro Gly Cys Gln Thr Cys Arg Tyr Leu Leu Val Arg Ser Leu
100              105                 110                 115

CAG ACG TTT AGT CAA GCT TGG TTT ACT TGC CGG AGG TGC TAC AGG GGC      441
Gln Thr Phe Ser Gln Ala Trp Phe Thr Cys Arg Arg Cys Tyr Arg Gly
                 120                 125                 130

AAC CTG GTT TCC ATC CAC AAC TTC AAT ATT AAT TAT CGA ATC CAG TGT      489
Asn Leu Val Ser Ile His Asn Phe Asn Ile Asn Tyr Arg Ile Gln Cys
             135                 140                 145

TCT GTC AGC GCG CTC AAC CAG GGT CAA GTC TGG ATT GGA GGC AGG ATC      537
Ser Val Ser Ala Leu Asn Gln Gly Gln Val Trp Ile Gly Gly Arg Ile
         150                 155                 160

ACA GGC TCG GGT CGC TGC AGA CGC TTT CAG TGG GTT GAC GGC AGC CGC      585
Thr Gly Ser Gly Arg Cys Arg Arg Phe Gln Trp Val Asp Gly Ser Arg
     165                 170                 175

TGG AAC TTT GCG TAC TGG GCT GCT CAC CAG CTG GTC CCG CGG TGG TCA      633
Trp Asn Phe Ala Tyr Trp Ala Ala His Gln Leu Val Pro Arg Trp Ser
180                  185                 190                 195

CTG CGT GGC CCT GTG TAC CCG AGG AGG CTA CTG GCG TCG AGC CAC TGC      681
Leu Arg Gly Pro Val Tyr Pro Arg Arg Leu Leu Ala Ser Ser His Cys
                 200                 205                 210

CTC AGA AGA CTT CCT TTC ATC TGT TCC TAC TGAGCTGGTC CCAGCCGACA        731
Leu Arg Arg Leu Pro Phe Ile Cys Ser Tyr
             215                 220

GTCCAGAGCT GCCCTCTCCT GGGCATGGCC TCCCCTCCTC TGCTTGCCAT CCCTCCCTCC    791

ACCTCCCTGC AATAAAATGG GTTTACTGA AAAAAAAAA AAAAAAAAA A                842
```